(12) United States Patent
Helm et al.

(10) Patent No.: US 11,903,751 B2
(45) Date of Patent: Feb. 20, 2024

(54) SYSTEM AND METHOD FOR DISPLAYING AN IMAGE

(71) Applicants: Medtronic Navigation, Inc., Louisville, CO (US); The Johns Hopkins University, Baltimore, MD (US)

(72) Inventors: Patrick A. Helm, Milton, MA (US); Jeffrey H. Siewerdsen, Baltimore, MD (US); Ali Uneri, Baltimore, MD (US)

(73) Assignees: Medtronic Navigation, Inc., Louisville, CO (US); The Johns Hopkins University, Baltimore, MD (US)

( * ) Notice: Subject to any disclaimer, the term of this patent is extended or adjusted under 35 U.S.C. 154(b) by 1100 days.

(21) Appl. No.: 16/375,327

(22) Filed: Apr. 4, 2019

(65) Prior Publication Data
US 2020/0315553 A1    Oct. 8, 2020

(51) Int. Cl.
A61B 6/12      (2006.01)
G06T 7/32      (2017.01)
A61B 6/00      (2006.01)
A61B 34/20     (2016.01)
A61B 34/10     (2016.01)

(52) U.S. Cl.
CPC ............. *A61B 6/12* (2013.01); *A61B 6/4035* (2013.01); *A61B 6/4078* (2013.01); *A61B 6/5241* (2013.01); *A61B 34/20* (2016.02); *G06T 7/32* (2017.01); *A61B 2034/102* (2016.02); *A61B 2034/2065* (2016.02); *G06T 2207/10081* (2013.01); *G06T 2207/10121* (2013.01); *G06T 2207/20221* (2013.01); *G06T 2207/30012* (2013.01)

(58) Field of Classification Search
None
See application file for complete search history.

(56) References Cited

U.S. PATENT DOCUMENTS

| 5,214,686 A * | 5/1993 | Webber ............... A61B 6/4233 |
| | | 378/98.2 |
| 9,098,896 B2 | 8/2015 | Barth et al. |
| 2003/0181809 A1 * | 9/2003 | Hall ........................ A61B 6/12 |
| | | 600/425 |

(Continued)

FOREIGN PATENT DOCUMENTS

| DE | 102015208929 B3 * | 6/2016 | ............... A61B 6/03 |
| JP | 2011508620 A | 3/2011 | |
| JP | 2017664 A | 1/2017 | |

OTHER PUBLICATIONS

International Preliminary Report on Patentability dated Oct. 15, 2020 in corresponding/related International Application No. PCT/US2019/026014.

(Continued)

*Primary Examiner* — Joseph M Santos Rodriguez
*Assistant Examiner* — Amy Shafqat
(74) *Attorney, Agent, or Firm* — Harness, Dickey & Pierce, P.L.C.

(57) ABSTRACT

A method and system is disclosed for analyzing and evaluating image data of a subject. The image data can be collected with an imaging system in a selected manner and/or motion. More than one projection may be combined to generate and create a selected view of the subject. The evaluation may be a location determination of a member positioned within the subject.

18 Claims, 9 Drawing Sheets

(56) References Cited

U.S. PATENT DOCUMENTS

| | | | |
|---|---|---|---|
| 2012/0289826 | A1 | 11/2012 | Graumann et al. |
| 2013/0070991 | A1 | 3/2013 | Yang et al. |
| 2014/0334709 | A1 | 11/2014 | Siewerdsen et al. |
| 2015/0178917 | A1 | 6/2015 | Yang et al. |
| 2016/0324499 | A1 | 11/2016 | Sen Sharma et al. |
| 2017/0165008 | A1* | 6/2017 | Finley .................. A61B 6/5235 |
| 2017/0231713 | A1 | 8/2017 | Siewerdsen et al. |
| 2018/0070902 | A1 | 3/2018 | Lin et al. |
| 2018/0250076 | A1* | 9/2018 | Gemmel .............. A61B 6/5205 |
| 2019/0384986 | A1* | 12/2019 | Chen ..................... G06V 40/67 |

OTHER PUBLICATIONS

European Office Action regarding Patent Application No. 197188840, dated May 10, 2022.
A Uneri et al, "3D-2D Known-Component Registration for Metal Artifact Reduction in Cone-Beam CT", The 5th International Conference on Image Formation in X-Ray Computed TOMOGRAPHY,May 20, 2018 (May 20, 2018), p. 151-155.
Ha Sungsoo et al, "Metal artifact reduction in CT via ray profile correction", Progress in Biomedical Optics and Imaging, SPIE—International Society for Optical Engineering, Bellingham, WA, US,vol. 9783, Mar. 31, 2016 (Mar. 31, 2016), p. 978334-978334.
International Search Report and Written Opinion dated Jul. 26, 2019 in corresponding/related International Application No. PCT/US2019/026014.
International Search Report and Written Opinion dated Sep. 7, 2020 in corresponding/related International Application No. PCT/US2020/026124.
Invitation to Pay Additional Fees dated Jul. 17, 2020 in corresponding/related International Application No. PCT/US2020/026124.
Newell, et al: "An intraoperative fluoroscopic method to accurately measure the post-implantation position of pedicle screws", International Journal of Computer Assisted Radiology and Surgery, Springer, DE, vol. 13, No. 8, Apr. 9, 2018, pp. 1257-1267, XP036559991, ISSN: 1861-6410, DOI: 10.1007/S11548-018-1732-8 [retrieved on Apr. 9, 2018].
Stayman J W et al, "Model-Based Tomographic Reconstruction of Objects Containing Known Components", IEEE Transactions on Medical Imaging, IEEE Service Center, Piscataway, NJ, US, vol. 31, No. 10, Oct. 2012 (Oct. 2012), p. 1837-1848.
Uneri, et al: "3D-2D image registration in virtual long-film imaging: application to spinal deformity correction", Progress in Biomedical Optics and Imaging, SPIE—International Society for Optical Engineering, Bellingham, WA, US, vol. 10951, Mar. 8, 2019, pp. 109511H-109511H, XP060121373, ISSN: 1605-7422, DOI: 10.1117/12.2513679, ISBN: 978-1-5106-0027-0.
Uneri, et al: "Known-component 3D-2D registration for quality assurance of spine surgery pedicle screw place", Physics in Medicine and Biology, Institute of Physics Publishing, Bristol GB, vol. 60, No. 20, Sep. 30, 2015, pp. 8007-8024, XP020289896, ISSN: 0031-9155, DOI: 10.1088/0031-9155/60/20/8007 [retrieved on Sep. 30, 2015].
Xu S et al, "Polyenergetic known-component CT reconstruction with unknown material compositions and unknown x-ray spectra", Physics in Medicine and Biology, Institute of Physics Publishing, Bristol GB, Mar. 28, 2017 (Mar. 28, 2017), vol. 62, No. 8, p. 3352-3374.
Japan Notice of Rejection corresponding to Japan Patent Application No. 2020-553543, dated Jan. 20, 2023.
Stayman J. W. et al., Model-based tomographic reconstruction of objects containing known components, Oct. 2010, IEEE Trans Medical Imaging, vol. 31, No. 10, pp. 1837-1848.
Xu S. et al., Polyenergetic known-component CT reconstruction with unknown with material compositions and unknown x-ray spectra, Mar. 28, 2017, Physics in Medicine & Biology, vol. 62, pp. 3352-3374.
Uenari A et al., Known-component 3D-2D registration for quality assurance of spine surgery pedicel screw placement, Oct. 21, 2015, Physics in Medicine & Biology, vol. 60, No. 20, pp. 8007-8024.
Ruth Veikko et al., Metal Artifact Reduction in X-ray Computed Tomography Using Computer-Aided Design Data of Implant as Prior Information, Jun. 2017, Investigative Radiology, vol. 52, No. 6, pp. 349-359.

* cited by examiner

SYSTEM AND METHOD FOR DISPLAYING AN IMAGE

FIELD

The present disclosure relates to imaging a subject, and particularly to a system to access image data for generating a selected view of the subject.

BACKGROUND

This section provides background information related to the present disclosure which is not necessarily prior art.

A subject, such as a human patient, may undergo a procedure. The procedure may include a surgical procedure to correct or augment an anatomy of the subject. The augmentation of the anatomy can include various procedures, such as movement or augmentation of bone, insertion of an implant (i.e. an implantable device), or other appropriate procedures.

A surgeon can perform the procedure on the subject with images of the subject that are based on projections of the subject. The images may be generated with imaging systems such as a magnetic resonance imaging (MRI) system, computed tomography (CT) system, fluoroscopy (e.g. C-Arm imaging systems), or other appropriate imaging systems.

SUMMARY

This section provides a general summary of the disclosure, and is not a comprehensive disclosure of its full scope or all of its features.

According to various embodiments, a system to acquire image data of a subject with an imaging system may use x-rays. The subject may be a living patient (e.g. a human patient). The subject may also be a non-living subject, such as an enclosure, a casing, etc. Accordingly, it is understood that appropriate subjects may be imaged. The imaging system may include a moveable source and/or detector that is moveable relative to the subject.

An imaging system may include a movable source and/or detector to generate or acquire one and/or a plurality of projections of a subject. The plurality of projections may be acquired in a linear path of movement of the source and/or detector. The plurality of projections may then be combined, such as by stitching together, to generate or form a long view (also referred to as a long film). The long view may be a two-dimensional view of the subject.

In various embodiments, the imaging system may acquire a plurality of projections at different perspectives relative to the subject. The different perspectives may be generated due to different paths of x-rays from a single source to the detector through the subject. A parallax effect exists and may allow for different views of the same position of the subject. The parallax effect may exist due to a filter having a plurality of slits or slots through which the x-rays pass and impinge upon the detector. Accordingly, movement of the source and/or detector relative to the subject may allow for acquisition of a plurality of projections through the subject including a parallax effect. The plurality of projections may then be stitched to form a plurality of long views of the subject due to movement of the source and/or detector.

Image data and/or images of a subject may also be acquired separate from an imaging system with a slotted filter. Further, images may be acquired at different time periods of the subject. The various images may also have differing dimensionality, such as three-dimensions (3D) or two-dimensions (2D). The different images, however, may be registered to one another. In various embodiments, the registration may allow for localization of members within the subject and/or localization of members within selected images.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
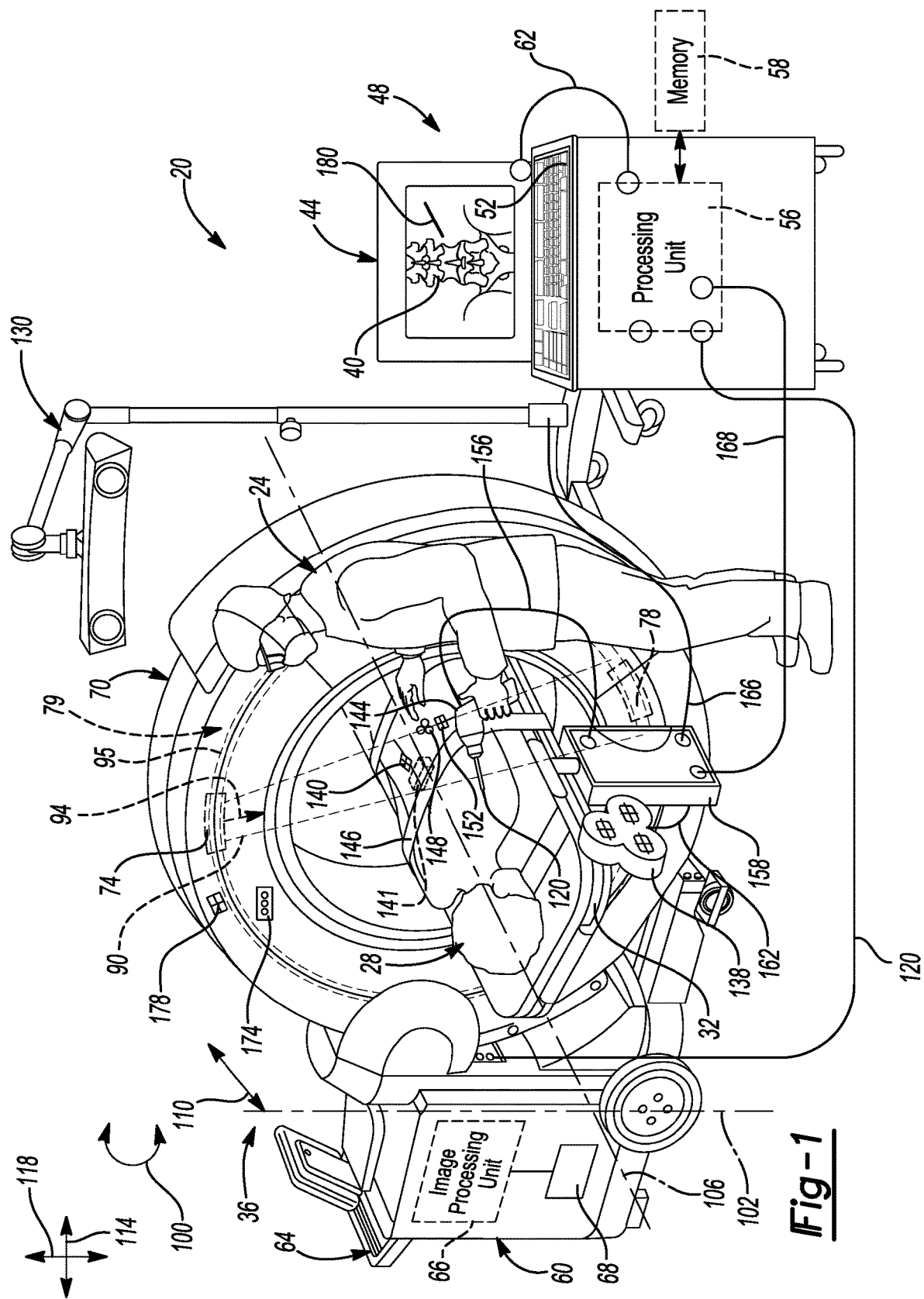
FIG. 1 is an environmental view of an imaging system in an operating theatre.

With reference to FIG. 1, a schematic view of a procedure room 20 is illustrated. A user 24, such as a surgeon, can perform a procedure on a subject, such as a patient 28. The subject may be placed on a support, such as a table 32 for a selected portion of the procedure. The table 32 may not interfere with image data acquisition with an imaging system 36. In performing the procedure, the user 24 can use the imaging system 36 to acquire image data of the patient 28 to allow a selected system to generate or create images to assist in performing a procedure. In various embodiments, the imagining system 36 may generate one or more projections of the patient 28 as image data thereof.

Images generated with the image data may include a model (such as a three-dimensional (3D) image), long views, single projections views, etc. can be generated using the image data and displayed as an image 40 on a display device 44. The display device 44 can be part of and/or connected to a processor system 48 that includes an input device 52, such as a keyboard, and a processor 56, which can include one or more processors or microprocessors incorporated with the processing system 48 along with selected types of non-transitory and/or transitory memory 58. A connection 62 can be provided between the processor 56 and the display device 44 for data communication to allow driving the display device 44 to display or illustrate the image 40. The processor 56 may be any appropriate type of processor such as a general purpose processor that executes instructions included in a program or an application specific processor such as an application specific integrated circuit.

The imaging system 36 can include an O-Arm® imaging system sold by Medtronic Navigation, Inc. having a place of business in Louisville, CO, USA. The imaging system 36, including the O-Arm® imaging system, or other appropriate imaging systems may be in use during a selected procedure, such as the imaging system described in U.S. Pat. Nos. 8,238,631; 9,411,057; and 9,807,860, all incorporated herein by reference.

The imaging system 36, when, for example, including the O-Arm® imaging system, may include a mobile cart 60 that includes a controller and/or control system 64. The control system 64 may include a processor and/or processor system 66 (similar to the processor 56) and a memory 68 (e.g. a non-transitory memory). The memory 68 may include various instructions that are executed by the processor 66 to control the imaging system 36, including various portions of the imaging system 36.

The imaging system 36 may include further additional portions, such as an imaging gantry 70 in which is positioned a source unit (also referred to as a source assembly) 74 and a detector unit (also referred to as a detector assembly) 78. The gantry 70 is moveably connected to the mobile cart 60. The gantry 70 may be O-shaped or toroid shaped, wherein the gantry 70 is substantially annular and includes walls that form a volume in which the source unit 74 and detector 78 may move. The mobile cart 60 may also be moved, and can be moved from one operating theater to another and or another room. The gantry 70 can move relative to the cart 60, as discussed further herein. This allows the imaging system 36 to be mobile and moveable relative to the subject 28 thus allowing it to be used in multiple locations and with multiple procedures without requiring a capital expenditure or space dedicated to a fixed imaging system.

The processor 66 may be a general purpose processor or a specific application processor. The memory system 68 may be a non-transitory memory such as a spinning disk or solid state non-volatile memory. In various embodiments, the memory system may include instructions to be executed by the processor 66 to perform functions and determine results, as discussed herein.

In various embodiments, the imaging system 36 may include an imaging system that acquires images and/or image data by the use of emitting x-rays and detecting interactions and/or attenuations of the x-rays with the subject 28. The x-rays emitted from the source 74 may be within a spectra and polyenergetic. Thus, x-ray imaging may be an imaging modality. It is understood that other imaging modalities are possible.

Figure 2:
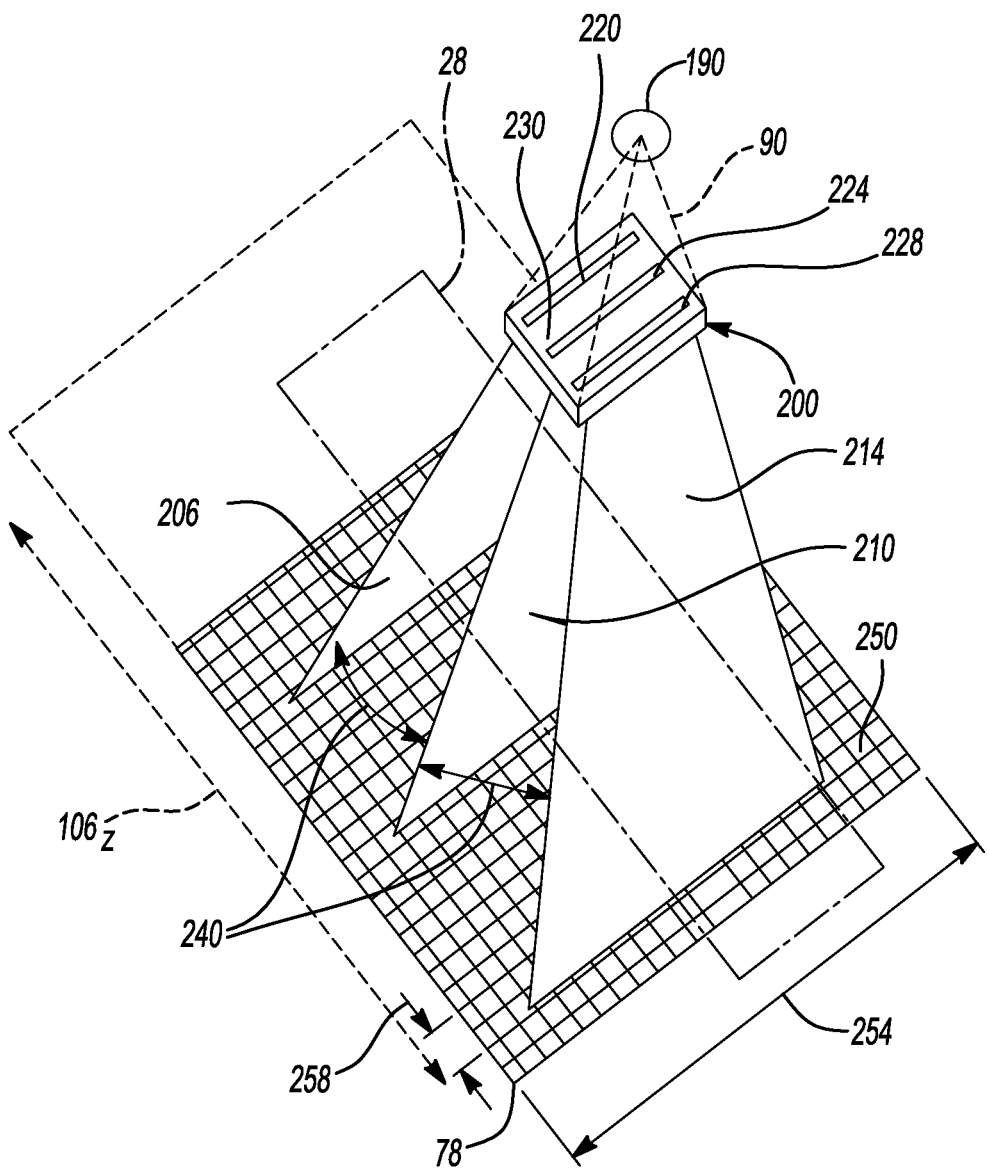
FIG. 2 is a top plan view of a slot filter body, according to various embodiments.

Thus, the imaging system 36 that includes the source unit 74 may be an x-ray emitter that can emit x-rays through the patient 28 to be detected by the detector 78. As is understood by one skilled in the art, the x-rays emitted by the source 74 can be emitted in a cone 90 along a selected main vector 94 and detected by the detector 78, as illustrated in FIG. 2. The source 74 and the detector 78 may also be referred to together as a source/detector unit 79, especially wherein the source 74 is generally diametrically opposed (e.g. 180 degrees apart) from the detector 78 within the gantry 70. The source 74 and the detector 78 may be mounted to a rotor and/or moveable on an internal track or movement assembly 95.

The imaging system 36 may move, as a whole or in part, relative to the subject 28. For example, the source 74 and the detector 78 can move in a 360° motion around the patient 28. The movement of the source/detector unit 98 within the gantry 70 may allow the source 74 to remain generally 180° opposed (such as with a fixed inner gantry or rotor or moving system) to the detector 78. Thus, the detector 78 may be referred to as moving around (e.g. in a circle or spiral) the subject 28 and it is understood that the source 74 is remaining opposed thereto, unless disclosed otherwise.

Also, the gantry 70 can move isometrically (also referred as "wag" relative to the subject 28 generally in the direction of arrow 100 around an axis 102, such as through the cart 60, as illustrated in FIG. 1. The gantry 34 can also tilt relative to a long axis 106 of the patient 28 illustrated by arrows 110. When tilting, a plane of the gantry 70 may tilt or form a non-orthogonal angle with the axis 106 of the subject 28.

The gantry 70 may also move longitudinally in the direction of arrows 114 along the line 106 relative to the subject 28 and/or the cart 60. Also, the cart 60 may move to move the gantry 70. Further, the gantry 70 can move up and down generally in the direction of arrows 118 relative to the cart 30 and/or the subject 28, generally transverse to the axis 106 and parallel with the axis 102.

The movement of the imaging system 60, in whole or in part is to allow for positioning of the source/detector unit (SDU) 79 relative to the subject 28. The imaging device 36 can be precisely controlled to move the SDU 79 relative to the subject 28 to generate precise image data of the subject 28. The imaging device 36 can be connected with the processor 56 via a connection 120, which can include a wired or wireless connection or physical media transfer from the imaging system 36 to the processor 56. Thus, image data collected with the imaging system 36 can be transferred to the processing system 56 for navigation, display, reconstruction, etc.

The source 74, as discussed herein, may include one or more sources of x-rays for imaging the subject 28. In various embodiments, the source 74 may include a single source that may be powered by more than one power source to generate and/or emit x-rays at different energy characteristics. Further, more than one x-ray source may be the source 74 that may be powered to emit x-rays with differing energy characteristics at selected times.

According to various embodiments, the imaging system 36 can be used with an un-navigated or navigated procedure. In a navigated procedure, a localizer and/or digitizer, including either or both of an optical localizer 130 and/or an electromagnetic localizer 138 can be used to generate a field and/or receive and/or send a signal within a navigation domain relative to the subject 28. The navigated space or navigational domain relative to the subject 28 can be registered to the image 40. Correlation, as understood in the art, is to allow registration of a navigation space defined within the navigational domain and an image space defined by the image 40. A patient tracker or dynamic reference frame (DRF) 140 can be connected to the subject 28 to allow for a dynamic registration and maintenance of registration of the subject 28 to the image 40. In various embodiments, the DRF 140 may be connected to and/or relative to a vertebra 141 within a spinal column of the subject 28.

The patient tracking device or dynamic registration device 140 and an instrument 144 can then be tracked relative to the subject 28 to allow for a navigated procedure. The instrument 144 can include a tracking device, such as an optical tracking device 148 and/or an electromagnetic tracking device 152 to allow for tracking of the instrument 144 with either or both of the optical localizer 130 or the electromagnetic localizer 138. Associated with the instrument 144 may be a second instrument (also referred to as an instrument), object, and/or member or implant 146. The implant 146 may also be tracked with the tracking system as it is connected to the instrument 144.

A navigation/probe interface device 158 may have communications (e.g. wired or wireless) with the instrument 144 (e.g. via a communication line 156), with the electromagnetic localizer 138 (e.g. via a communication line 162), and/or the optical localizer 130 (e.g. via a communication line 166). The interface 158 can also communicate with the processor 56 with a communication line 168 and may communicate information (e.g. signals) regarding the various items connected to the interface 158. It will be understood that any of the communication lines can be wired, wireless, physical media transmission or movement, or any other appropriate communication. Nevertheless, the appropriate communication systems can be provided with the respective localizers to allow for tracking of the instrument 144 relative to the subject 28 to allow for illustration of a tracked location of the instrument 144 relative to the image 40 for performing a procedure.

One skilled in the art will understand that the instrument 144 and/or member 146 may be any appropriate instrument, such as a ventricular or vascular stent, spinal implant, neurological stent or stimulator, ablation device, or the like. The instrument 144, 146 can be an interventional instrument or can include or be an implantable device. Tracking the instrument 144, 146 allows for viewing a location (including x,y,z position and orientation) of the instrument 144, 146 relative to the subject 28 with use of the registered image 40 without direct viewing of the instrument 144, 146 within the subject 28. Further, discussion herein of the instrument 144 may be understood to reference to any tracked member, such as the instrument 146, unless specifically indicated otherwise.

Further, the imaging system 36, such as the gantry 70, can include an optical tracking device 174 and/or an electromagnetic tracking device 178 to be tracked with the respective optical localizer 130 and/or electromagnetic localizer 138. Accordingly, the imaging device 36 can be tracked relative to the subject 28 as can the instrument 144 to allow for initial registration, automatic registration, or continued registration of the subject 28 relative to the image 40. Registration and navigated procedures are discussed in the above incorporated U.S. Pat. No. 8,238,631, incorporated herein by reference. Upon registration and tracking of the instrument 144, an icon 180 may be displayed relative to, including overlaid on, the image 40.

With continuing reference to FIG. 1 and additional reference to FIG. 2, according to various embodiments, the source 74 can include a single x-ray tube assembly 190. As discussed above, x-rays can be emitted from the x-ray tube 190 generally in the cone shape 90 towards the detector 78 and generally in the direction from the x-ray tube 190 as indicated by arrow, beam arrow, beam or vector 94. The vector 94 may be a central vector or ray within the cone 90 of x-rays. An x-ray beam may be emitted as the cone 90 or other appropriate geometry. The vector 94 may include a selected line or axis relevant for further interaction with the beam, such as with a filter member, as discussed further herein.

The subject 28 can be positioned within the x-ray cone 94 to allow for acquiring image data of the subject 28 based upon the emission of x-rays in the direction of vector 94 towards the detector 78.

The x-ray tube 190 may be used to generate one or more two dimension (2D) x-ray projections of the subject 28, including selected portions of the subject 28, or any area, region or volume of interest, in light of the x-rays impinging upon or being detected on a 2D or flat panel detector, as the detector 78. Generally, more than one 2D x-ray projections can be reconstructed, as discussed herein, to generate and/or display three-dimensional (3D) volumetric models of the subject 28, selected portion of the subject 28, or any area, region or volume of interest. As discussed herein, the 2D x-ray projections can be image data acquired with the imaging system 36, while the 3D volumetric models can be generated or model image data.

For reconstructing or forming the 3D volumetric image, appropriate algebraic techniques include Expectation maximization (EM), Ordered Subsets EM (OS-EM), Simultaneous Algebraic Reconstruction Technique (SART), Total Variation Minimization (TVM), filtered back projection (FBP) (e.g. Feldkamp-Davis-Kress algorithm reconstruction), model based iterative reconstruction, and others as generally understood by those skilled in the art. The application to perform a 3D volumetric reconstruction based on the 2D projections allows for efficient and complete volumetric reconstruction.

In various embodiments, an algebraic technique can include an iterative process to perform a reconstruction of the subject 28 for display as the image 40. For example, a pure or theoretical image data projection, such as those based on or generated from an atlas or stylized model of a "theoretical" patient, can be iteratively changed until the theoretical projection images match the acquired 2D projection image data of the subject 28. Then, the stylized model can be appropriately altered as the 3D volumetric reconstruction model of the acquired 2D projection image data of the selected subject 28 and can be used in a surgical intervention, such as navigation, diagnosis, or planning. The theoretical model can be associated with theoretical image data to construct the theoretical model. In this way, the model or the image data 40 can be built based upon image data acquired of the subject 28 with the imaging device 36.

The source 74 may include various elements or features that may be moved relative to the x-ray tube 190. In various embodiments, for example, a collimator may be positioned relative to the x-ray tube 190 to assist in forming and/or shaping the cone 90 relative to the subject 28. The collimator may include various features such as movable members that may assist in positioning one or more filters within the cone 90 of the x-rays prior to reaching the subject 28. In various embodiments, the members may include a filter, such as a slotted or three slotted filter 200. In various embodiments, as discussed herein, the x-ray beam 90 may be formed or split into a plurality of beams or into one or more thin fans or planes (e.g. 206, 210, 214) that reach and pass through the subject 28 and be detected by the detector 78. The collimator and/or filter portions, including the imaging system 36, may include those disclosed in U.S. Pat. No. 10,881,371 issued Jan. 5, 2021 (U.S. patent application Ser. No. 16/233,753; filed Dec. 27, 2018), incorporated herein by reference.

The filter 200 may include a selected number of slots or passages, such as including three slots including a first edge slot 220, a middle slot 224, and a second edge slot 228. Each of the three slots 220, 224, 228 may be formed through the filter 200 in an appropriate manner, such as electrical-discharge machining or other appropriate tool (e.g. a router or punch). It is further understood that the slots may be forged or otherwise cut into the filter 200.

In various embodiments, near or at a first surface 230 each of the three slots 220, 224, 228 are formed by two respective side walls each. The side walls for each of the slots 220, 224, 228 are generally equal distances apart and substantially parallel along the length of the respective slots. Further, the slot walls are generally straight and parallel relative to one another. It is understood, however, that certain tooling cause various portions of the slots to be of a slightly different dimension, such as an entry or exit plunge cut to initiate or end the slot. However, each of the slots 220, 224, 228 are generally formed to have a dimension between the sidewalls of about 0.001 in to about 0.1 in, including about 0.009 in to about 0.03 in, and further including about 0.025 in to about 0.01 in, and further including about 0.02 in (about 0.5 mm). The dimension of the slots 220, 224, 228 may be substantially identical for each of the slots is generally a dimension between the interior surfaces of the respective opposed walls of the respective slots.

A central axis may be defined through each of the slots 220, 224, 228. The central axis of the middle slot 224 may be substantially normal to a plane of the detector 78. The edge slots 220 and 228, however, may have respective central axes that extend substantially parallel to the respective side walls and not perpendicular to the surface 230 and/or detector. These slots, therefore, would split the beam 90 into the three fans 206, 210, and 214. The two external or edge fans would form an angle 240 relative to the central fan 210. The angle 240 may be about 5 degrees to about 10 degrees and further about 6 degrees to about 8 degrees, and further about 7 degrees.

The angles may assist in allowing x-rays to pass from the source 190, as schematically illustrated in FIG. 2, through the respective slots 220-228 without any or substantial distortion due to interaction with the respective side walls. As illustrated in FIG. 2 and as discussed above, the x-rays may be emitted from the source tube 190 in substantially a cone shape. Accordingly, x-rays that travel substantially normal to the surface 230 will pass through the central slot 224 along the central axis without substantial or any interaction with the side walls forming the slot 224. Also due to the respective angles, the x-rays that are near an edge of the cone 90 may pass through the edge slots 220, 228 without substantial interaction with the respective side walls due to the respective angles of the slots.

The slot filter member 200 may allow for a formation of three x-ray fans or areas of x-rays including the first fan 206, the second fan 210, and the third fan 210 due to the respective slots 220-228. In other words, the slot filter 200 filters the x-rays from the source 190 and allows the x-rays to pass through the slots 220-228 to form the fans 206-214. In various embodiments, the slot filter assembly 200 is a selected distance from the source 190. The distance may be about 50 mm to about 100 mm, including about 60 mm to about 80 mm, further including about 68 mm to about 72 mm.

As discussed further herein, the three fans 206-214 allow for generation of selected image projections due to an imaging area on the detector 78. It is further understood that the numbering of the slots 220-228 and the respective fans 206-214 is merely for clarity of the current discussion, and not intended to require any particular order. Further, it is understood, that the filter member 200 may include a selected number of slots, such as less than three or more than three and three is illustrated and discussed for the current disclosure. It is understood, however, that the three slots allow for the generation of a long view in an efficient and fast manner, as discussed further herein. Including a selected different number of slots may allow for a generation of a different number of intermediate images as discussed herein, but is not required.

The entire cone 90 from the source 74 may have an area that would excite or impinge upon the entire surface of the detector 78. However, the individual fans 206-214 generally impinge upon only a narrow band of pixels 250. It is understood that the number of pixels excited may include an entire width 254 of the detector 78, but limited to only a selected length 258 of the detector. For example, the respective fans 206-214 may impinge upon, assuming that no object or subject is within the path of the x-rays (e.g. an air scan), about 10 about 100 pixels. The number of pixels excited in the dimension 258 on the detector 78, however, may be augmented or adjusted depending upon the distance from the detector 78 of the filter assembly 200, the width of the slots (220-228), or other appropriate considerations. Nevertheless, as illustrated in FIG. 2, each of the respective fans 206-214 will impinge upon the detector 78 at a substantially narrow position and excite a length 258 of pixels that may be along a substantially entire width 254 of the detector 78. The width of the slots 220-228 that causes the length of pixels 258 to be excited (e.g. generate image data) limits or eliminates parallax distortion within the image portion collected with the imaging system using the slot filter 200, as discussed herein.

Further, as illustrated in FIG. 2, the detector 78 may be impinged upon by the three fans 206-214 substantially simultaneously from a single position of the source tube 190 along the Z-axis generally in the direction of the double headed arrow 106z. The Z-axis may be, in various embodiments, aligned or parallel with the long axis 106 of the subject 28. The detector 78, therefore, may output three different images or image data for three different positions of the x-ray at each single position of the source tube 190. Movement of the source tube 190 of the source 74 generally in the direction of the double headed arrow 114, however, may create a plurality of three views along the Z-axis, as discussed further herein. Each of the fans 206-214 may be separated by a selected distance, which may also be an angular distance 240.

The imaging system 36 may be used to generate images of the subject 28, for various purposes. As discussed above, the images may be generated of the subject 28 for performing a procedure on the subject 28, such as a spinal fusion and/or implants relative to or adjunct to a spinal fusion. In various embodiments, therefore, user 24 may evaluate the subject 28 by viewing and evaluating images of the subject 28 for determination of placement of selected implants, such as pedicle screws. Accordingly, the imaging system 36 may be used to acquire an image of the subject 28. The image system 36 may be used to acquire one or a plurality of projections. As further discussed above, the detector 78 detects x-rays that pass through or are attenuated by the subject 28. Generally, however, the detector 78 detects a single projection at a time. The imaging system 36, including the control system 64, either alone or in combination with the processor system 48 may generate a long film or long view of the subject 28 by accumulating (e.g. stitching) a plurality of projections of the subject 28. In various embodiments, the imaging system 36, therefore, may be operated to acquire a plurality of images.

In addition to the images that may be acquired of the subject 28 with the imaging system 36, additional and/or alternative image data images of a subject 28 may be obtained and/or accessed. For example, the subject 28 may be imaged with a selected imaging system that may acquire and/or reconstruct three-dimensional (3D) image or model of the subject 28. The images may be used for various purposes, as discussed further herein, to assist in performing a procedure on the subject 28 and/or analyzing a procedure performed on the subject 28.

In various embodiments the 3D image data of the subject 28 may be acquired with computed tomography (CT) imaging system, a magnetic resonance (MR) imaging system, or other appropriate imaging system. Generally, the imaging systems may acquire image data of the subject 28 to allow for reconstruction of a 3D image for analysis and/or visualization of the subject 28. The 3D image or model may be acquired and/or generated at a selected time, such as prior to a procedure. The 3D image, therefore, may be stored in a selected memory such as the memory 58 or other appropriate accessible memory.

Figure 3:
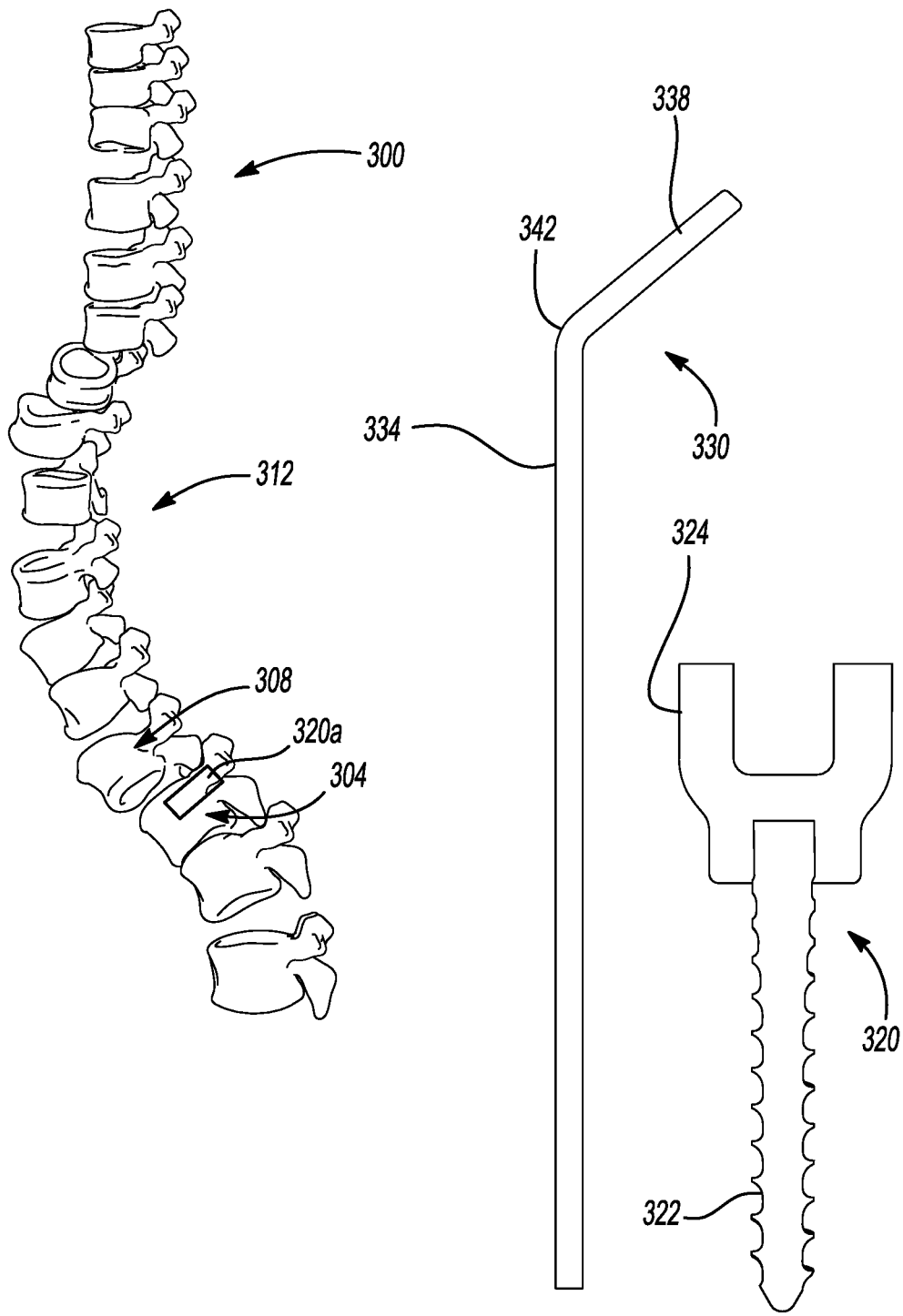
FIG. 3 is a view of a 3D image and a member.

The 3D image may be generated in any appropriate manner, such as with the imaging techniques as discussed above. With reference to FIG. 3, a 3D image 300 may be displayed on the display device 44 as the image 40 or on any appropriate image display. Further, the image 300 may be stored in the memory 58 for recall for various purposes, as selected or discussed further herein, including registration to a later acquired image. The image 300 may include image data of an entire subject (e.g. an entire spine of a patient) and/or a portion of the anatomy of the subject 28, such as a region of interest (ROI) of the subject, including one or more vertebrae of the subject 28. For example, the image or image data 300 may include image data of a first vertebrae 304 and a second vertebrae 308. It is understood, however, that the image 300 may include image data of all of the vertebrae of the subject 28.

In various embodiments, the subject 28 may have a selected or diagnosis, such as scoliosis. Accordingly, a portion of the image 300 may include a diagnosed feature, such as a scoliotic portion 312. It is understood, however, that all of the vertebrae relative to a diagnosed concern may be imaged and included in the image 300.

The image 300 may be a three-dimensional image of the subject 28, including the spine of the subject. Accordingly, the image 300 may include image data of the plurality of vertebrae, such as the first and second vertebrae 304, 308 in at least three-dimensions. It is understood that a plurality of images may be acquired to illustrate the three-dimensional nature of the imaged portion as it changes over time. However, in the following discussion, it is understood that the image 300 may be a three-dimensional image that is used to analyze and/or compare to later acquired images.

In various embodiments, for example, the image 300 may be acquired of the subject 28 for diagnosing the subject 28. Further the image 300 may be used to plan a selected procedure relative to the subject 28. For example, to perform a procedure on the subject 28 may include positioning one or more screws, such as a pedicle screw 320 into one or more of the vertebrae, such as the second vertebrae 308. The screw 320 may include a shank portion 322 and a head portion 324. The head portion 324 may be movable relative to the shank portion 322. The screw 320 may include CD Horizon® Solara® or Legacy® spinal or pedicle screws, sold by Medtronic, Inc. having a place of business in Minnesota, USA. In addition to the screw, a rod or fixation member 330 may be used. The rod 330 may also be similar to a rod or portion used with the CD Horizon® spinal fixation system. The rod 330 may be positioned between a plurality of the screws 320 that are fixed within the subject 28 to hold the respective vertebrae in a selected position relative to one another. The rod 330 may be locked within the head 324 in an appropriate manner, such as with a locking or set screw.

At a selected period, such as prior to performing a surgical procedure on the subject 28, the image 300 may be acquired and analyzed by a selected user, such as the user 24. During a planning procedure, positioning of one or more of the screws 320 within the vertebrae, such as relative to the vertebrae 304, may be determined. In various embodiments, an icon or graphical representation of the screw 320 may be displayed on the image 300 as a screw representation 320*a*. Accordingly, the user 24 may plan positions for one or more of the screws 320 in the subject such as on the 3D model 300. The user 24 may also plan a selected geometry of the rod 330 for interconnecting a plurality of the screws. For example, the rod 330 may include at least two portions such as a first elongated portion 334 and a second elongated or curved portion 338. A bend or curved portion 342 may interconnect the respective elongated portions 334, 338.

Nevertheless, the 3D image 300 of the subject 28 may be acquired for various purposes, such as planning a procedure relative to the subject 28. The acquired image 300 may then be saved in a selected memory, such as the memory 58, for recall at a selected time that is after the acquisition and storing of the image 300. For example, as discussed further herein, the image system 36 may acquire an image which may be compared to the 3D image 300.

The user 34, may then perform a procedure on the subject 28. The procedure performed on the subject may be any appropriate procedure and may be based upon the plan that may use the image 300 and/or various alternative thereto. Regardless, the user 34 may perform a procedure on the patient 28.

In various embodiments, the procedure may include positioning one or more of the screws 320 into the subject 28. During the procedure, the user 34 may position a selected number of the screws in one or more of the vertebrae 304, 308 of the subject 28. After a selected period of time, such as after positioning all of the screws identified in the plan, an image may be acquired of the subject 28. In various embodiments, the imaging system 36 may be used to acquire one or more projections of the subject 28. As discussed above, the projections may be generated with the imaging system 36 in any appropriate manner. Generally, the projections may be acquired of the subject 28 in a substantially two-dimensional manner and at different positions relative to the subject 28.

Figure 4:
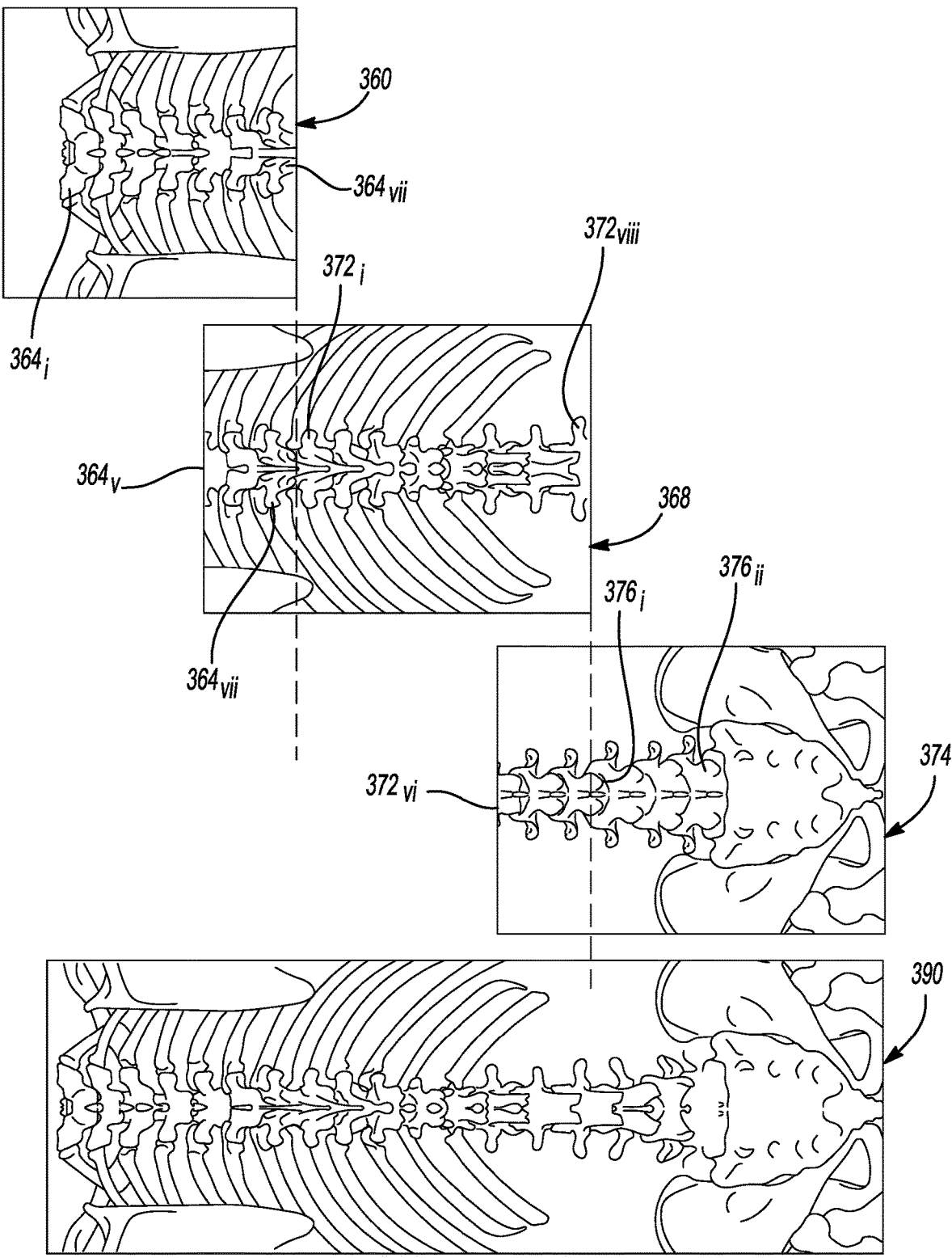
FIG. 4 is a view of 2D image.

With continuing reference to FIGS. 1 and 2 and additional reference to FIG. 4, the imaging system 36 may acquire a plurality of projections by moving relative to the subject 28, such as discussed above along the long axis 106 of the subject generally along a Z-axis 106*z*. The images acquired may be any appropriate type of images, such as with or without the slotted filter 200. That various selected slot projections (i.e. generated by the fan beam of x-rays) may be stitched together into selected long views, such as a first or projection long view 360, that may include images of a plurality of vertebrae such as seven vertebrae in a projection including projection or stitched vertebrae 364*i* to 364*vii*. In various embodiments, for example with a filter including a single slot, a single one projection or stitched projection may be viewed or generated. The first view 360 may be a short or partial long view that may be formed by stitching together a plurality of projections from one or more of the slots, such as the slot 220 acquired as the source 190 moves relative to the subject 28.

However, as discussed above, the filter 200 may include a plurality of the slots 220-228 thus allowing for the generation of a plurality of projections along the Z-axis 106*z*. Accordingly, a second or projection long view 368 may include a selected number of vertebrae including overlap vertebrae 364v, 364vi, and 364vii. Additionally the image projection 368 may include an additional plurality of vertebrae including 372i to 372viii. Accordingly, the second image projection 368 may include images of 11 vertebrae. Finally, a third or projection long view 374 may include a plurality of vertebrae projection images including the vertebrae 372vi, 372vii, and 372viii. The third projection 374 may, however, further include additional vertebrae or portions of the subject including vertebrae 376i and 376ii.

Each of the individual projection long views 360, 368, 374 may be formed, such as by stitching, of a plurality of projections generated by the fans 206-214 on the detector 78 collected as the source 190 moves relative to the subject 28, such as by movement of the gantry 70. Thus, each of the individual projection long views 360, 368, 374 may be stitched together from selected and/or separate projections of the subject 28.

In various embodiments, the plurality of individual or separate long stitched projections 360, 368, 374, may be stitched into a single very long or extended film or projection 390. Each of the individual projection long views 360, 368, 374 may also be referred to as constituent views or constituent long views. In various embodiments, the long view 390 may be formed based on a weighted stitching of the shorter or individual long views 360, 368, 374 that accounts for the portion of the subject most or best imaged in the individual long views 360, 368, 374 (e.g. including more superior portions of more inferior portions of the subject 28).

In the various images or image data, including the stitched images 360, 368, 374, and the extended film 390, the image is of the subject 28 may generally be collected during or after a procedure, such as a portion of a procedure. For example, the subject including the vertebrae 141, may be viewed in a visualization or view, such as based on the extended long view 390. It is understood, however, that discussion herein of the long view 390 is merely exemplary and that any appropriate views may be used as discussed herein.

Regardless, the long view 390 may be generated of the subject 28 during a selected portion of a procedure and may include the vertebrae 141 which may be identified as vertebrae 141i. As discussed above, the vertebrae 141i may be identified in the long view 390 through various mechanisms, such as anatomical reconstruction, image analysis, or the like. Further, as discussed above, between the various views or long films 360, 368, 374, overlap various anatomical portions or portions in the image may be identified. These overlaps may allow for stitching the various views together. Moreover, more than one view, such as two substantially orthogonal views, may be generated of the subject 28. Accordingly, the vertebrae 141 may be determined in a three-dimensional space based upon a plurality of the long views.

Moreover, as discussed above, the implant 146 may be positioned within the subject, which may include the screw 320. As the long view 390 is acquired after performing a portion of a procedure, an image 320i of the screw may also be identified. It is understood that a plurality of the screws may be included in the long view 390 such as the first screw 320i and a second screw 320'i. It is understood that any appropriate number of screws may be viewed in the image 390 and the number in the image or long view 390 may be based upon the number positioned in the subject 28.

Regardless of the number of the screws in the subject 28 that are imaged in the long view 390, the screws may be identified in the image including both of their geometry therein and their three-dimensional position. As discussed further herein, the three-dimensional image 300 of the subject 28 may be acquired of the subject 28 prior to performing any procedure on the subject 28. Accordingly, the three-dimensional image 300 may not include any objects, such as the screws 320, therein. Nevertheless, the three-dimensional image 300 may be of the same portion of the anatomy (e.g. ROI) or any appropriate portion of any appropriate subject, as a long film 390. As discussed further herein, a registration may be made between the long film 390 and the three-dimensional image 300. Based upon a registration of the long film 390 with the three-dimensional film 300, a determination of a location of the screws, such as the screws in the image 320i and 320'i, may then be correlated to the three-dimensional image from the long view 390 to identify an actual placement of the screw in the subject 28 that relates the three-dimensional image 300 and/or comparison to a planned position of the screw, such as the planned position 320a.

Figure 5:
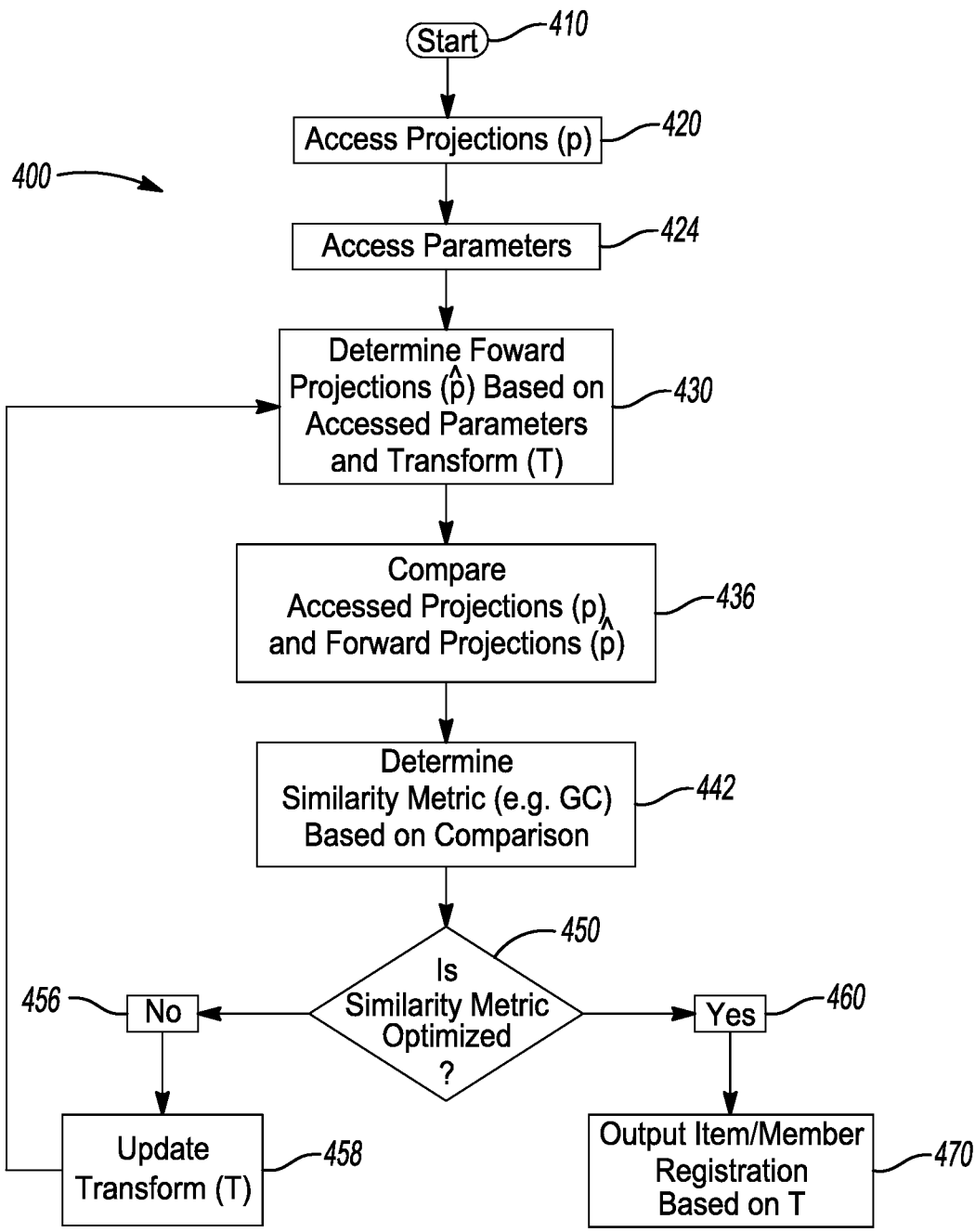
FIG. 5 is a flowchart for a process of member/component registration.

With continuing reference to FIG. 3 and FIG. 4, and additional reference to FIG. 5 the image of the screw 320i and 320'i may be identified in the long image 390 according to a process 400 of registering or determining a location of the screw in the image, such as a long field image 390. The process 400 may include various processes including a parameters process, wherein the parameters may include known components of the implants, such as the screw 320, to identify the screw in the image 390. The known components may be used to minimize or reduce metal artifacts in a final visualization of the long film 390. It is understood, however, that any appropriate determination of the screw image 320i and 320'i in the image 390 may be made, such as determining a location of the screw in the image long view 390 and with the registration correlating it to the 3D view 300.

The process or flowchart 400 illustrates a process, which may be efficient and/or quick, for determining a location of a member (also referred to as a component or an item), such as the screw image 320i in the image 390. In various embodiments, the process 400 may be used to remove artifacts from a visualization, but may also be used to determine the location of the item for various purposes. The process 400 allows for an efficient, including lower computational time and/or necessary resources, to determine the substantially precise location of an item in the image and/or generate a visualization. In various embodiments, the visitation may be inclusive of the long film 390.

The pedicle screw 320 may be formed of one or more selected material (e.g. metal or metal alloy) that affects x-rays when generating x-ray image data in a manner to cause distortion or artifacts relative to the x-rays that generate the image data of the vertebrae 141. Therefore the process 400 may be used to remove or account for the artifacts in the image data when generating the image 40 for display with the display device 44. It is further understood that the pedicle screw 320, or other selected item, may be formed of or include a plurality of materials.

With continued reference to FIG. 5, the process 400 is understood to be an image analysis and/or reconstruction process 400 that may be performed alone and/or in part of a selected procedure, such as a surgical procedure including positioning the pedicle screw 320 in the vertebrae 141. The process 400, therefore, may also be an algorithm, or include algorithmic portions, that may be executed by a selected processor or processor system, such as the imaging processing unit 56 discussed above. It is understood, however, that any appropriate processing system may be used to execute the process 400 to generate an image for display on the display device 44.

As discussed above, various procedures may occur relative to the subject 28. In various embodiments, the pedicle screw 320 may be placed in the subject 28. Thus, projections may be acquired of the subject 28 with one or more of the pedicle screws implanted therein. The projections maybe acquired, as discussed above, and then accessed at a selected time in block 420.

Any appropriate selected number of projections, however, may be acquired and accessed in the process 400. For example, the projections illustrated in FIG. 4 may be included. It is further understood, however, that the stitched long views may also be accessed as the projections and may be stitched prior to the process 400.

The projections in block 420 may include an input for the process 400. Additional inputs may include parameters, such as known component parameters or known components (KC), in block 424. The parameters in block 424 may be generally known or predetermined parameters. The parameters may be used to define the component (as noted above also referred to as the member or the item). The component or member may include the screw 320. The item or member in the subject 28 being a screw is merely exemplary, and discussion herein to the screw 320 is not intended to limit the scope of the subject disclosure or appended claims.

The parameters may be predetermined parameters of the selected item, such as the pedicle screw 320. In various embodiments, for example, the parameters may include specific features of the item, such as the pedicle screw 320. For example, the screw 320 including the shank 322 and the head 324. The parameters may further include the type of material of the selected portions of the pedicle screw 320, such as the shank 322 formed of a stainless steel alloy and the head 324 being formed of the same stainless steel alloy. Parameters may further include selected dimensions such as length, width, height, and the like. Parameters in block 424 may also include a range of motion and/or degree of freedom of motion (e.g. possible geometries) of the shank 322 relative to the head 324. The parameters may also account or be known regarding the imaging modality, such as a polyenergetic x-ray beam, or other features.

In various embodiments, therefore, the parameters in block 424 may be representations, such as a lookup table, of the selected item including the pedicle screw 320. Further, the known parameters in block 424 may include selected specific models, such as a computer aided design (CAD) model of the pedicle screw 320 including known materials thereof and known interactions of x-rays relative thereto. In various embodiments, the pedicle screw 320 is the CD Horizon® Solara® implantable pedicle screw and the parameters in block 424 may include a CAD model of the specific pedicle screw (including a specific model number and/or geometry and dimensions thereof) or a deformable spline model (such as a spline model of a cylindrical wire, needle, or rod) along with known materials, known interaction of materials, and the like. The known parameters in block 424 may then be accessed, such as recalled with the processing unit 56, for further portions of the process 400.

With the accessed projections in block 420 and the accessed parameters in block 424, a registration or location determination may occur. The registration may include various steps or processes, as discussed herein. In various embodiments, a forward projection is generated in block 430 based on the known parameters in block 424 which may also be referred to as a component projection. The forward projection in block 430, as discussed further herein, may then be compared in block 436 to the accessed projections from block 420. Based upon the comparison in block 436 a similarity metric (which may include a gradient correlation (GC)) may be determined in block 442. The comparison in block 436, yielding the similarity metric in block 442, may then be optimized in block 450.

In the optimized determination block 450, a transformation may be generated that is again applied to a forward projection in block 430 if a determination is made that the GC is not optimized by following a NO path 456. Once the GC is determined to be optimized, a YES path 460 may be followed to provide a registration or location output of the item in block 470.

An optimized transformation, when following the YES path 460, may be a convergence where the differences between the forward projection in block 430 and the projections in block 420 are substantially small or have a selected similarity metric in block 450. At the selected transformation of similarity metric, the transformation is determined to have converged or been optimized as an optimized transform ($\hat{T}$) and may be used for registration and determination of a location of the item in the image, such as the image 390. In various embodiments, a reconstruction may also be performed of the image 390 with the registered parameters of the item.

The registration process 400 includes a registration of the parameters from block 424 with a selected number of projections, including less than or all of the acquired projections from block 420, that may be used for a later reconstruction and/or visualization. In particular, the registration is to determine the portion in the acquired projections from block 420 that match to the parameters in block 424 that may include the known component definition of the item, such as the screw 320. For example, one or more pixels in one or more of the projections are generated by the selected item (e.g. pedicle screw 320) that is imaged in the subject 28 in the projections 420 and, therefore, should match the determined forward projection in block 430 of the known component from block 424. For example, as discussed above, the pedicle screw 320 may have precise or determined parameters, for example predetermined parameters that define the parameters in block 424.

The parameters may be input as represented by k. A forward projection may be determined as a digital radiograph reconstruction or digitally reconstructed radiograph (DRR) forms the forward projection in block 430 and may be defined by Equation 1 (Eq. 1):

$$\hat{p}(k,T) = \int_r k(T) d\vec{r} \qquad \text{Eq. 1}$$

In Eq. 1, the forward projection $\hat{p}$ is a projection based on the parameters from block 424. In particular, Eq. 1 is formed from the input parameters κ from block 424, which may include a mesh model of the selected item that is a line integral along a ray $\vec{r}$ incident on the transformed parameters κ. Accordingly, the forward projection $\hat{p}$ is a digitally reconstructed radiograph (also referred to as a mask herein) based upon the parameters κ from block 424 that may be compared to the accessed projections (also referred to herein as p). One or more selected transformation models (T) may be employed, such as a rigid homogeneous transform or a deformable b-spline function. Generally, only one transformation model may be selected in any specific application, but various appropriate models may be selected or the transformation (T). Furthermore, select sets or limited parameters κ may be included within the optimization process, for example to model the unknown diameter of a tool with a cylindrical profile.

The forward projection as determined in block 430 may be compared in block 436 to the accessed projections p from block 420. The comparison in block 436 allows for an output or determination of the similarity metric which, in various embodiments, is defined as a gradient correlation (GC) as defined in Equation 2 (Eq. 2) in block 442. While GC is an appropriate similarity metric, it is understood that other similarity metrics may also be used. Regarding GC, Eq. 2 is:

$$GC(p,\hat{p}) = \tfrac{1}{2}\{NCC(\nabla_x p, \nabla_x \hat{p}) + NCC(\nabla_y p, \nabla_y \hat{p})\} \quad \text{Eq. 2}$$

and NCC is defined in Equation 3 (Eq. 3):

$$NCC(a, b) = \frac{\sum_i (a_i - \bar{a})(b_i - \bar{b})}{\sqrt{\sum_i (a_i - \bar{a})^2} \sqrt{\sum_i (b_i - \bar{b})^2}} \quad \text{Eq. 3}$$

The GC generally looks for gradients (also referred to as high contrast regions or edges) between the forward projection $\hat{p}$ in block 430 and the accessed projections in block 420. According to Eq. 2 and Eq. 3, the GC is defined as a sum of a normalized cross-correlation (NCC) of orthogonal image gradients. For example, the NCC defines the correlation of the normalized intensities of image gradients a and b for images p and $\hat{p}$, respectively. Therefore, the GC, as defined in Eq. 2, is a sum of the gradients between the forward projection from block 430 and the accessed projections from block 420.

In block 450 a determination may be made of whether the GC is optimized. In making the determination, the maximum or convergence of transform $\hat{T}$ has been found or achieved. In particular, the convergence is defined by Equation 4 (Eq. 4):

$$\hat{T} = \underset{T}{\arg\max} \sum_\theta GC(p_\theta, \hat{p}_\theta(\kappa, T)) \quad \text{Eq. 4}$$

which may be iteratively solved between the forward projection in block 430 and the accessed projections from block 420. Eq. 4 is used to determine the greatest similarity between the forward projection in block 430 and the accessed projections in block 420. The iteration occurs by determining the GC in block 442 based upon the comparison in block 436 and then determining whether the GC is optimized in block 450. Accordingly, the optimizer block 450 may determine whether the similarly metric in block 442 is the same or has been optimized and/or within a selected threshold of change, for example when the mean change in T is smaller than about 0.01 millimeters (mm) to about 0.2 mm, including about 0.1 mm and about 0.01 degrees to about 0.2 degrees, including about 0.1 degrees. The threshold may also or alternatively include a specific value, such as when changes in the similarity metric GC approach the machine precision (such as an image processing unit 56) for representing floating-point numbers.

If the optimizer in block 450 determines that a threshold has not been reached, then a NO path 456 may be followed to update a transform T in block 458 that may be applied when generating the forward projection determined forward projection in block 430. The forward projection may then be altered, such as by altering (e.g. rotating or translating) the component or member when determining a forward projection. In other words, a different perspective of the component, as defined by the known component, in block 430 may be used to form a new forward projection for comparison to the acquired projections from block 436. If the optimizer block 450 determines at a convergence has been achieved (e.g. a difference from a present GC is within a threshold relative to a prior GC) then the converged or optimized transform T may be output with the YES path 460.

Appropriate optimization techniques may be used in the optimizer block 450, such as those that may be executed by the processing unit 56, or other appropriate processing unit. In various embodiments, a covariance matrix adaptation evolution strategy may be used to achieve the optimization in block 450. The selected strategy may include a stochastic derivative free optimization method. It is understood, however, that other appropriate optimization methods or techniques may be used in the optimizer block 450.

Once the YES path 460 is followed, the optimized transformation ($\hat{T}$) may be output in block 470. The optimized transformation may also be referred to as a registration, as discussed herein, to allow for a determination of a location of the item (e.g. the screw 320) in space. In various embodiments, the optimized location may also be used to determine the 3D position of the item even if the accessed projections are in two dimensions (2D).

Figure 6:
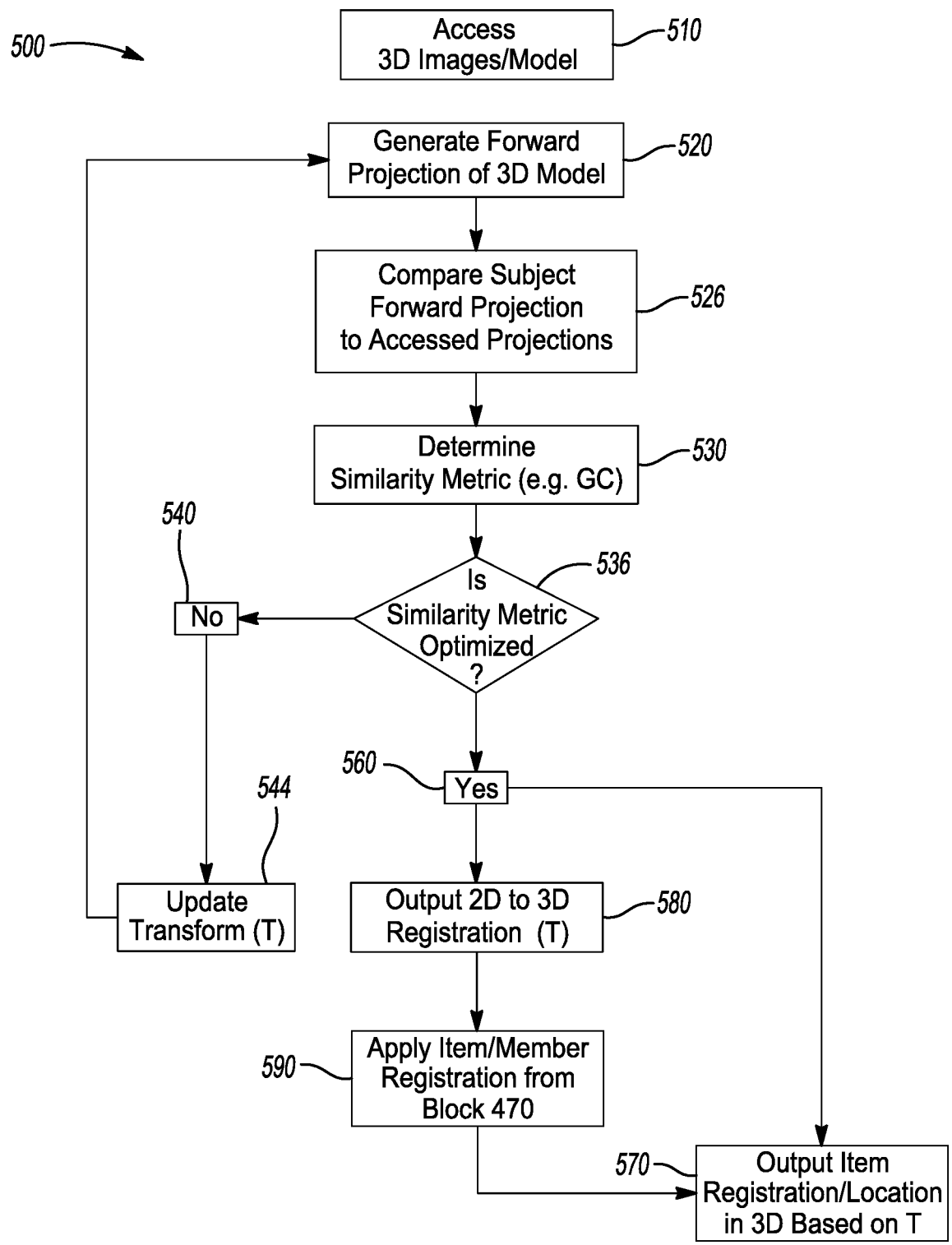
FIG. 6 is a flowchart for a process for subject image registration.

With continuing reference to FIG. 5 and additional reference to FIG. 6, a registration of the output member registration 470 to the three-dimensional image 300, may be performed according to the process 500 as illustrated in FIG. 6. The registration process or localization in three-dimensions may include evaluating the accessed projections in block 420 and the output registration in block 470. In various embodiments, the accessed projections in block 420 may be registered to the forward projection from the three-dimensional image 300. According to the process 500, the 3D image 300 may be accessed in block 510. After accessing the 3D image in block 510, generation of a projection, such as a subject forward projection, may be made in block 520. The generation forward projection 520 may be based upon various calculations including Equation 5 (Eq. 5):

$$\int_r P(r)dr \quad \text{(Eq. 5)}$$

Generating forward projections may be based upon any appropriate calculation, such as those generally understood in the art. In various embodiments, however, the forward projection may be defined by an integral of a projection along a ray r through the patient image P. The patient image P may be the three dimensional model 300 as discussed above. Once the forward projection is generated in block 520, a comparison of the subject forward projections to the accessed projections is made in block 526. As discussed above, the accessed projections may be the projection accessed in block 420, as discussed above. Accordingly the accessed projections may be based upon the generation or collection of image data during a selected procedure, such as with the imaging system 36. The imaging system 36 may generate a plurality of projections of the subject 28, which may be substantially 2D projections of the subject. In various embodiments, the projections may include projections that are collected of the subject 28 from an x-ray emission that is collected on the detector 78, or other appropriate projections. As also discussed further herein the projections, may include a plurality of fan being or thin projections generated with the slotted filter 200 to generate various long films, such as the long film 390.

In various embodiments, the subject forward projection from block 520 may be compared to the accessed projections in block 526. A determination of a similarity metric may then be made. The similarity metric may include a gradient orientation (GO) in block 530. In determining the similarity metric in block 530, appropriate techniques may include determining a similarity between the forward projections and the accessed projections in block 420. The similarity metric GO may be similar to the similarity metric GC, as discussed herein, and similar techniques may be used to determine the similarity between the subject forward projections generated in block 520 and the accessed projections in block 420.

Once the similarity metric is determined in block 530, a determination of whether the similarity metric is optimized may be made in block 536. As discussed above, the determination of the optimization may include a calculation of a maximization of the similarity metric. In various embodiments, the optimization may be defined by Equation 6 (Eq. 6):

$$\hat{T}_P^O = \underset{T}{\arg\max} \sum_\theta GO\left(P_\theta, \int_{\vec{r}} P(\vec{r})d\vec{r}\right) \quad \text{(Eq. 6)}$$

The optimization may include a summation of or maximization of the similarity metric GO, including after rotating the image (e.g. the 3D model 300) when generating the forward projections and are defined to translation thereof. $P_\theta$ is the accessed projections at the angle $\theta$ and $P(\vec{r})$ is a projection through the 3D image of the subject 300, previously defined.

If the similarity metric is not optimized or determined to be optimized in block 536 a NO path 450 may be followed. In following the NO path 540, a transformation may be generated in block 544. The generated transformation may include an alternative or different rotation and/or translation of the image 300 when generating a forward projection in block 520. Accordingly, the optimization process may be an integrative process to maximize the similarity metric. Various techniques may be used to determine the optimization such as a covariance matrix adaptation evolution strategy or process to optimize the rotation to achieve the optimization in block 536.

Similar to the process discussed above, in various embodiments, the determination of the optimization may also include a determination of a location of the item, such as the screw 320, in the three-dimensional view 300. According to Equation 7 (Eq. 7):

$$\hat{\lambda} = \underset{\lambda}{\arg\max} \sum_\phi GC(VLF_\phi, P_\phi[\kappa(\lambda)]) \quad \text{(Eq. 7)}$$

an optimization or registration of the screw in the 3D image may be based upon an optimization of a pose or location parameter $\lambda$ of the item (e.g. the screw 320). In Eq. 7 the similarity metric may include a gradient correlation (GC) between the accessed projections, such as the projections acquired with the slotted filter, at an angle $\phi$ represented as $VLF_\phi$. $P_\phi[k(\lambda)]$ is the accessed projections at the angle $\phi$ with the parameters $\kappa$ at a selected posed or location parameter $\lambda$. Accordingly, the output item member registration in block 470 may be incorporated into Eq. 7 as the last term to determine a registration of the 2D image (including the item, such as the screw 320) and the prior 3D image 300. The process for optimization of Eq. 7 may include various techniques such as the covariance matrix adaptation evolution strategy, as discussed above, to optimize various parameters, such as the posed or location parameter $\lambda$ of the item. Accordingly, the location may be determined directly from the 2D projections and illustrated relative to the 3D view of the subject, which may be prior acquired, such as prior to positioning the item within the subject (e.g. the screw 320).

Regardless of the optimization technique or direct registration, once the similarity metric is optimized in block 536, a YES path 560 may be followed to output the item registration or location in 3D in block 570. The output of the item registration may be used or include a determination of the location of the item, such as the screw 320, in three-dimensional space. In other words, the location of the item (e.g. screw 320) in the 2D image (e.g. long view 390) may be correlated to a location in the 3D image (e.g. 3D model 300). The determination of the item in three-dimensional space may begin its use for various purposes, as discussed further herein. Moreover, the discussion herein to the illustration and determination of the screw 320 and/or portions thereof in three-dimensional space is merely exemplary and not intended to limit the disclosure herein or appendant claims.

In various embodiments, as discussed above, the optimization performed in block 536 may include or yield a 2D to 3D registration, including a registration of the accessed 3D image 300 and the accessed projections in block 420. Accordingly, following the YES path may initially perform or output the 2D to 3D registration in block 580. The 2D to 3D registration may include the registration as discussed above and may be output separately, such as initially, from a YES block 560 to register the 2D image (e.g. 2D image space) to the 3D image (e.g. 3D image space). The item or member registration from block 470 may be applied to the output 2D to 3D registration in block 590. By applying the item or member registration from block 470, which is registered to the 2D accessed projection in block 420, the 2D to 3D registration from block 580 may allow for an output of an item registration or location in 3D in block 570. Accordingly, the registration or localization of the item in a three-dimensional position, according to the process 500, may be performed in an appropriate manner including (i) registering 2D projections (e.g. the accessed projection from block 420) after registering or locating the item therein and/or (ii) determining a similarity or optimizing a similarity between a three-dimensional image and the forward projections of at least the item based upon known components or parameters thereof.

The long film or long view, such as the long view 390, therefore may include the image of the screw 320$i$ and 320'$i$ as the long view 390 is generated by stitching together a plurality of projections, such as fan or slot projections, of the subject 28 after positioning the implant therein. As noted above, the implant may be any appropriate item, such as the screw 320. Further, as discussed above, the projections generated by the slotted filter 200 may be at an angle relative to the source 190 and relative to other slots. Accordingly, the plurality of projections acquired with the slotted filter 200 may define a parallax between different projections to allow for determination of a location of the item (e.g. the screw 320) as imaged in the image, such as a long view 390.

In various embodiments, to perform the registration with Eq. 7, a knowledge or predetermination of the position of the respective projections acquired with the individual slots may be used when performing a stitching of the various projections to form the long view 390. As illustrated in FIG. 4, the long view 390 may be a combination of the three shorter long views 360, 368, 374 that are formed due to single ones of the slots of the slotted filter 200. Accordingly, various selected functions may be used to generate the long view 390, such as a weighted function, where the portion of the long view 390 is generated from a slot view or projection most related to the position of the long view 390. Accordingly, as illustrated in FIG. 4, the vertebrae 364*i* may be generated from the view 360 and the long view 390 based substantially on the view 360 rather than the other long views 368, 374. The generation of the long view 390, therefore, may be produced substantially with reduced or minimized parallax distortion due to the slot of the slotted filter 200, as disclosed in U.S. Pat. No. 10,881,371 issued Jan. 5, 2021 (U.S. patent application Ser. No. 16/233,753, filed Dec. 27, 2018), incorporated herein by reference.

Figure 7:
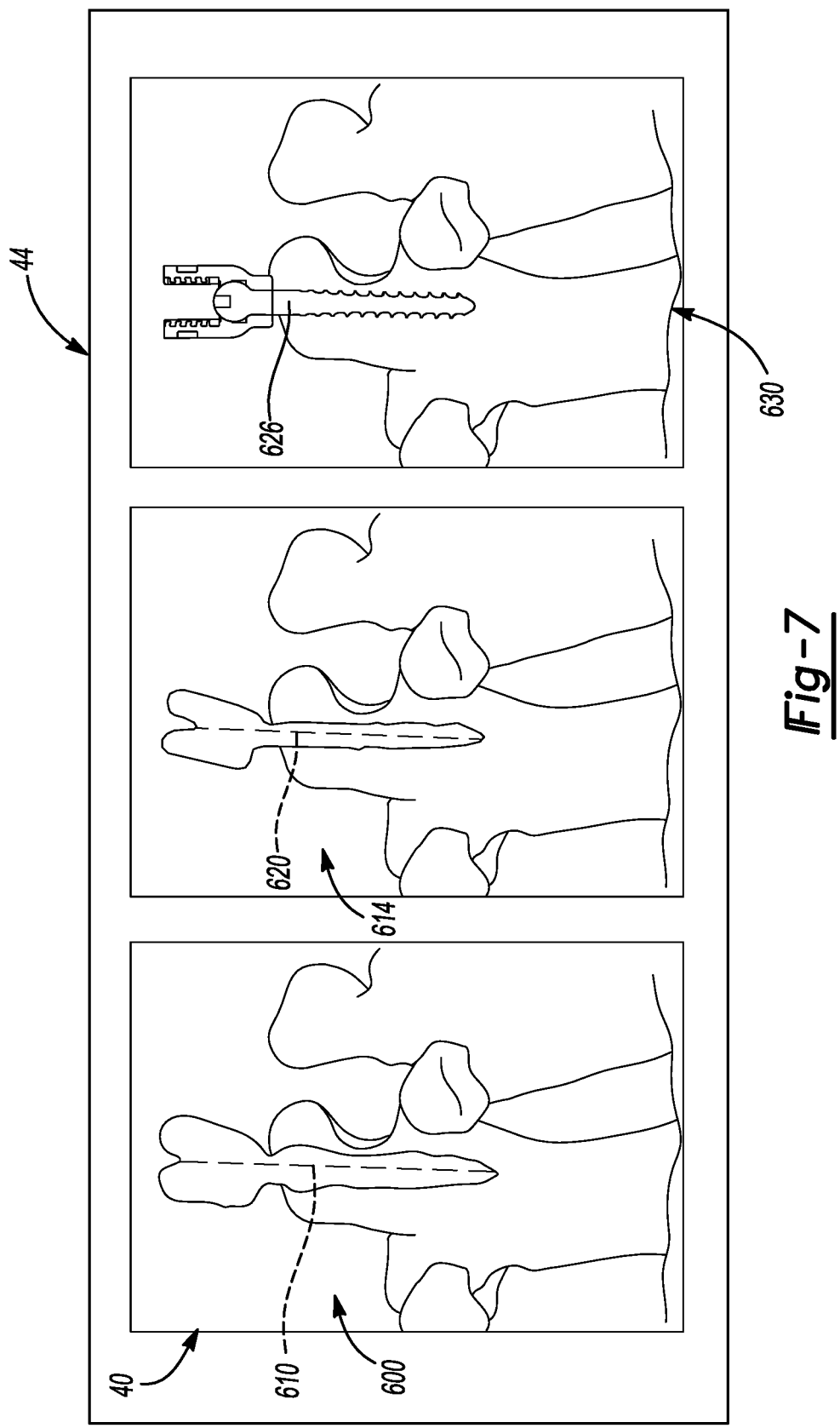
FIG. 7 is a 2D view of a representation of a registered location of the member.

Regardless of the technique for registration, including those discussed above, the position of the item such as the screw 320 may be illustrated and/or represented relative to images or reconstructions as a visualization as illustrated in FIG. 7. The representation may include an overlay or superimposition of a graphic and/or altering the image display. The display device 44 may display the image 40, including a plurality of images 40, to represent the location in the 3D image or space.

Once the user 24 has operated the system to complete the registration, the visualization may include various features such as illustrating one or more projections of the subject 28, such as a fourth lumbar left side visualization image 600 that includes a prime or main axis 610 of the screw 320. The main axis 610 may be illustrated to the user 24 to understand the registered position of the implant 320. Additional visualizations may also be provided, such as of a right side of a first lumbar vertebrae in image 614 including a main axis 620. Additional and/or alternative visualizations may include an overlay or super imposition of a graphical representation 626 of the screw 320 on an image or visualization portion 630.

The various representations, including the axis representation 610, 620 and/or graphical representation 626 may be used by the user 24 to understand the registered (i.e. correlated) position of the implant 320 to one or more positions of the subject 28. As discussed above, the 3D image 300 may be used by the user 24 for planning a procedure, such as by placing a planned location image 320*a*. The images 40, including the various visualizations 600, 614, 630, may be compared to and/or overlaid on the planned position of the image 300. Accordingly, the display 44 may, in addition to or alternatively to the image 40, display the 3D image as a registered image display 650, as illustrated in FIG. 8.

Figure 8:
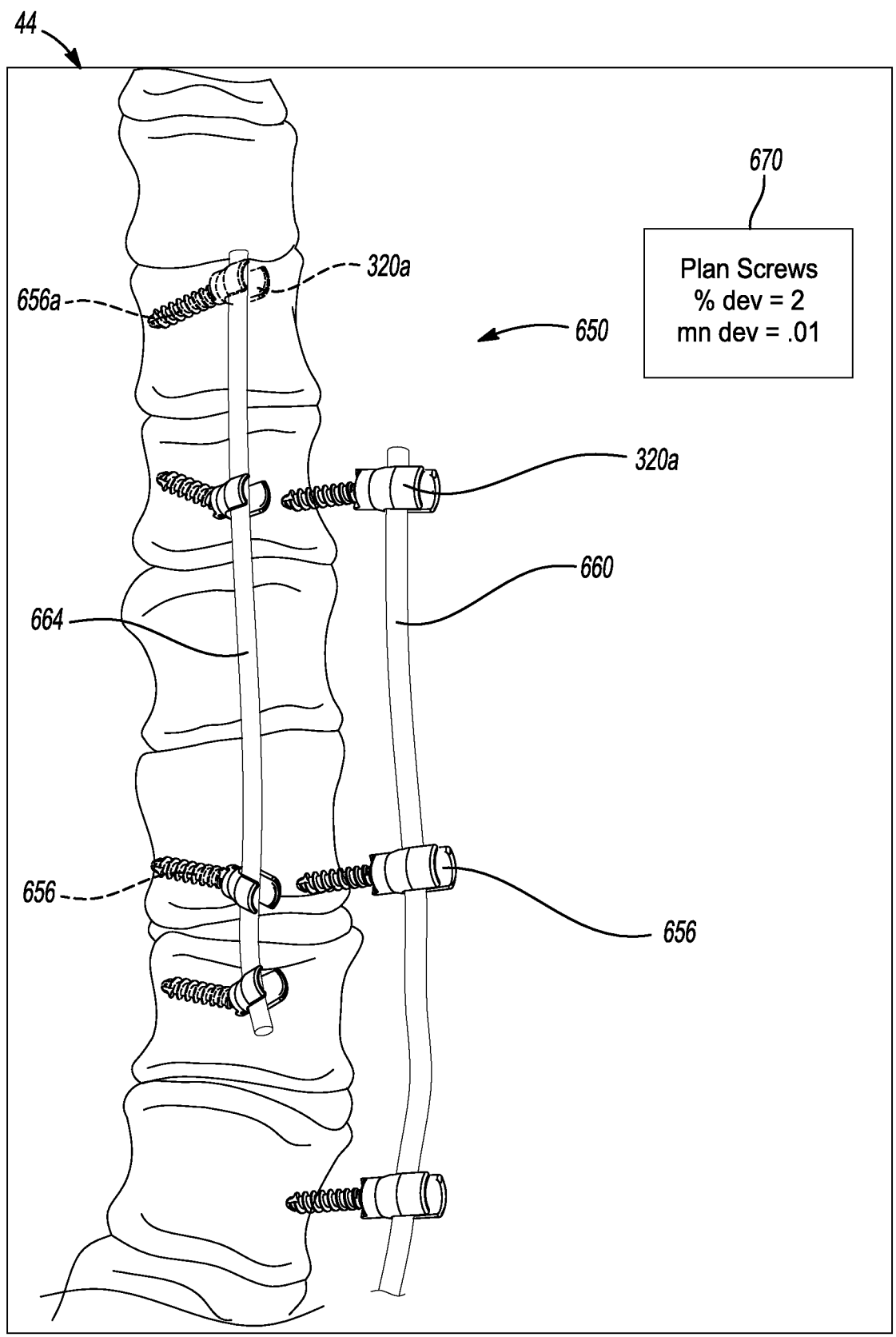
FIG. 8 is a 3D view of a representation of a registered location of the member.

As illustrated in FIG. 8, the 3D image 300 may be displayed with the planned position 320*a* and the registered positions of the screws 320 on an image 650. Accordingly, the image 650 may include the 3D image 300, which may be acquired prior to a procedure. As discussed above, the 3D image 300 may be based upon or include a CT image, MR image, or other appropriate 3D images. Nevertheless, the registered location of the screws 320 may be illustrated as icons or graphical representations 656 superimposed on the image 300 in the registered location image 650. Each of the registered screw representations 656 may be superimposed on the 3D image or included in the registered image 650 to assist the user 24 in visualizing or understanding the location of the implanted screws relative to a planned position, and a final position of the screws 320.

As illustrated in FIG. 8, the visualizations of the screws may include representations for every screw that is implanted into the subject 28. For example, eight screws may be included within the registered image 650 representing eight screws that are positioned in the patient 28. Although eight screws are illustrated in FIG. 8, it is understood that any appropriate number of screws may be included including less than or more than eight. The user 34 may view the display device 44 to view the visualization of the subject 28 including the representation of the screws 656.

In various embodiments, the system may execute further instructions to connect the screw representations 656 such as including a first line or rod 660 and a second line or rod 664. In various embodiments, rods may be used to interconnect selected screws to achieve a selected or desired outcome or shape of the spine of the subject 28. For example, the subject 28 may be diagnosed with a spinal deformity such as scoliosis. Implanting the screws 320 and connecting them with a selected shaped rod may be used to attempt to achieve a selected or desired spine shape outcome. Accordingly the shape of the rod 660, 664 may be illustrated on the registered image 650 including connection of the identified or registered screw heads of the screw representation 656. However, as discussed further herein, the registered position of the screws in the registered image 650 may be used to define or determine a shape of a rod to move the screws (and associated anatomy) during placement of the rod 330 to achieve a selected outcome.

Further, as discussed above, the registered image 650 may include one or more representations 320*a*. The representation 320*a* may be the planned position of the screw, such as the screw 656*a* illustrated in FIG. 8. The registered location of the screw 656*a* may be compared to the planned position 320*a*. The user may view the registered image 650 including both representations including the registered representation 656*a* and the planned position 320*a* to determine success of the procedure relative to the plan.

In addition to visualization by the user 24, the system, such as the work station 48, may execute instructions with the processor 56 to measure or determine a main axis of the registered screw, as discussed above, and a main axis of the planned screw position 320*a*. The axis of the planned position 320*a* may be predetermined or known based on the known geometry of the panned screw 320. An information screen, such as a plan success or information display 670, may be illustrated on the display device 44. The display box 670 may illustrate a representation of the determined position of the implanted screw relative to the planned position. For example, a percent deviation and/or distance deviation may be illustrated in the display 670 to provide information to the user 24 regarding a difference between the planned position and the implanted positions.

In light of the above, therefore, the visualizations illustrated in FIGS. 7 and 8, may be generated without requiring a secondary or post procedure three-dimensional scan of the subject. For example, as noted above, the imaging system 36 may acquire projections and/or generate the long film or a stitched long film of the subject 28 that may be based upon a plurality of two-dimensional projections. Accordingly, a radiation dose to the subject 28 and/or individuals near the imaging system 36 may be reduced or minimized due to the single view (e.g. AP and/or lateral) scans. The confirmation or registration visualizations 650, therefore, may be used by the user 34 to confirm and/or plan further procedure steps while minimizing radiation to the subject 28 and to individuals near the imaging system.

In various embodiments, for example, the registration image 650 may be displayed on the display device 44 in various manners, such as in a substantially three-dimensional view as illustrated in FIG. 8 and/or in selected projections as illustrated in FIG. 7. It is understood that the various images illustrated in FIG. 7 may be displayed simultaneously on the display device 44 with the registration image 650 and/or alternatively thereto. Further, the images, including the images 600, 614, and 630 may also be referred to as registration images regarding the displayed portion therein.

Accordingly, a procedure and/or plan may be confirmed by viewing the registration image 650 that is substantially three-dimensional and portions thereof. In various embodiments, the registration image may be displayed as portions thereof or augmented, such as viewing the graphical representation of the screw 626 and/or a long axis or main axis of the screw, such as the axis 610. The user 24 may view the registered positions of the screws for various purposes, such as confirming the procedure and/or performing or planning subsequent procedure portions.

Figure 9:
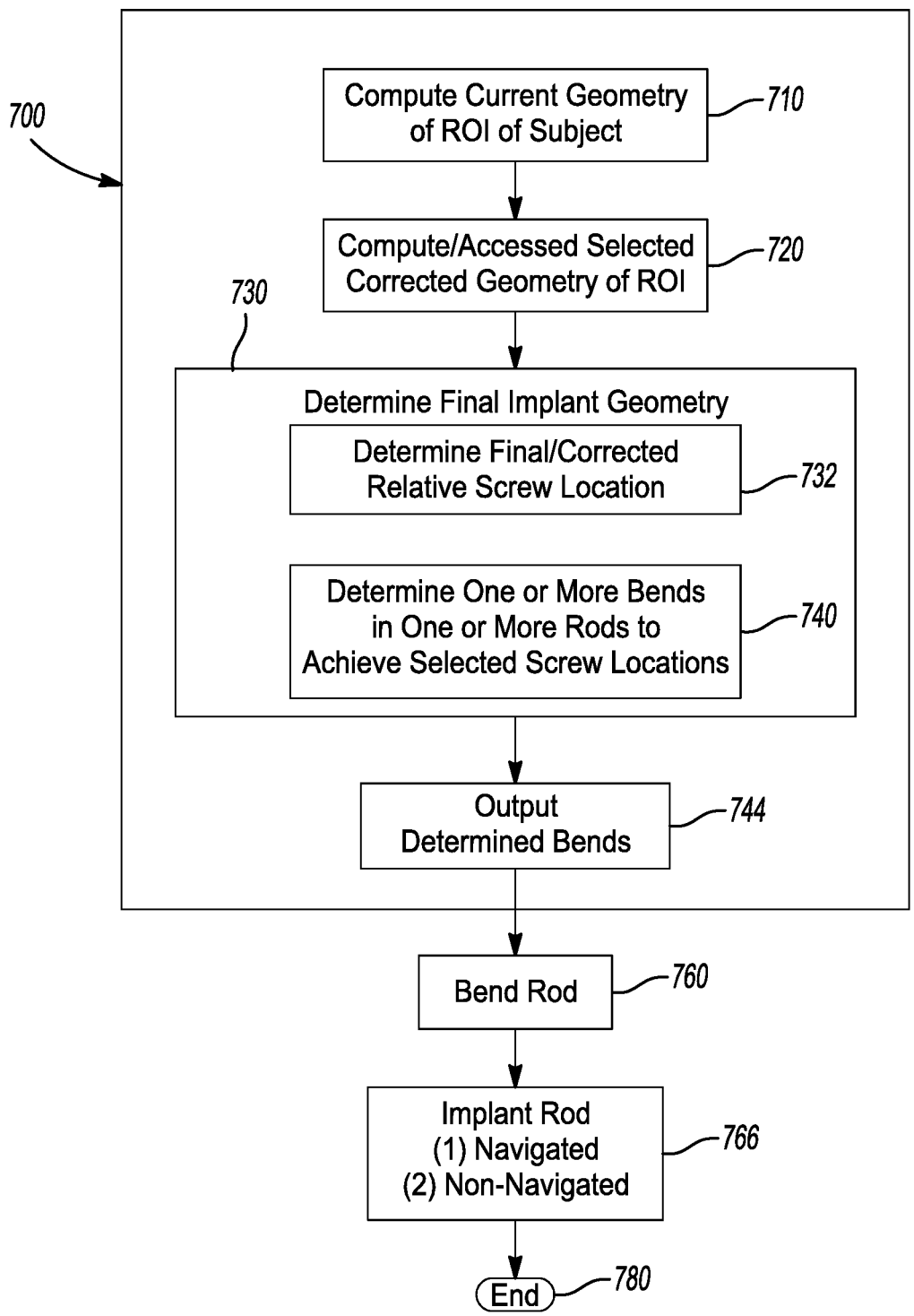
FIG. 9 is a flowchart for a process of defining a shape of a member based on a first member registration.

In various embodiments, after placing the screws 320 a rod shape may be determined to achieve or attempt to achieve a selected outcome of the subject 28. For example, with reference to FIG. 9, a process 700 may be used to plan or determine a geometry of the rod 330 for implantation which may or may not be illustrated as the rod 660, 664. In various embodiments, the rod 330 may be defined between two terminal ends to interconnect the plurality of screw implanted in the subject 28. For example, the eight screws may be implanted on a left and right side of the subject to be interconnected by a selected rod. The selected one or more rods that connect the left set of screws and the right set of screws, separately, may be designed and shaped to achieve a selected shape of the spine of the subject after implantation and fixation of the rod. Accordingly, once the screws are implanted, the region of interest of the subject may include a spine of the subject.

A geometry of the spine of the subject, which may be the region of interest of a subject, may be computed according to the process 700 in block 710. Computing the geometry may include identifying the various boney structures of the spine in the image and/or based upon the registered screws. As discussed above, a main or primary axis of each of the screws may be identified, such as the axis 610. Accordingly, a geometry or position in space between the relative main axes, such as the main axis 610 and the main axis 620 may be calculated. The geometry between or defined by the registered screws in the registration image 650 may be used to determine the geometry or shape of the spine. Thus, the determination of a current and/or selected final or corrected geometry may be based on at least the registration of the location of the screws in the 3D model, as discussed above. The screws, therefore, may be used to determine the geometry of the spine and are, therefore, also determined or located.

The current geometry (e.g. morphology or curvature) of the region of interest may therefore be determined by calculating a spatial difference between each of the screws in a selected set. For example, a geometry between each of the left screws and right screws may be calculated to determine a geometry of the region of interests in block 710.

A selected and/or computed selected corrected geometry of the region of interest, such as the spine, may be computed and/or accessed in block 720. In various embodiments, a selected corrected geometry may include a geometry of the spine in the preoperative configuration or with substantially no alteration. Accordingly, the selected corrected geometry may be the geometry of the patient's spine. For example, a degenerative bone or disc disease may be identified and the screws 230 connected by a selected ride may be used to maintain a current shape of the spine.

However, in various embodiments, the subject 28 may be diagnosed with a spinal deformity. For example, scoliosis may include a non-selected or non-optimal curve of the spine. Thus, the selected corrected geometry computed in block 720 may include a selected movement of the spinal vertebrae to achieve a final selected geometry of the spine. The final or corrected geometry may be calculated based on the current geometry, such as determined by the determined and registered location of the implanted screws. Also, the user 24 may determine or pre-define a selected or determined final geometry and the predetermined, (e.g. user defined or determined) geometry may be recalled or accessed in block 720. In various embodiments, an analysis of global spinal alignment (GSA) may be made and may be pertinent to assessment of spinal curvature and related metric. Specific GSA measures may include sagittal alignment (SA), thoracic kyphosis (TK). Additional and/or alternative measures of global spinal curvature may be assessed in terms of "Cobb" angles, pelvic incidence (PI), and pelvic tilt (PT).

Once the computed and/or accessed selected corrected geometry is made in block 720, a determination of a final implant placement and/or geometry may be made in block 730. As discussed herein, the final geometry may include a final relative screw location in block 732 and rod geometry (e.g. bends) may be made in block 740. The final relative screw location may include a selected location and/or movement (e.g. move superiorly 2 mm or laterally 5 mm) of a screw to achieve the selected corrected geometry from block 720. As discussed above, the registered positions of the screws may be used as a surrogate or for determining the position of each of the vertebrae in the spine. Accordingly, selecting a location for a screw to achieve a selected corrected geometry may be calculated in block 732. All of the right side screws may be calculated to have a selected final geometry relative to one another to achieve a selected corrected geometry of the region of interest, including the spine. For example, if a most superior and most inferior screw are substantially aligned and intermediate screws are out of alignment, a computation may be to include the intermediate screws more in alignment with the superior and inferior screws. Thus, the computation may be made to determine a selected amount of movement relative to a superior to inferior axis of the subject 28 to achieve the selected corrected geometry from block 720. The processor system 56 may compute the selected location based upon attempting to achieve a more axial position or selected position of the spine after connection of the plurality of screws with a rod. For example, the processor system 56 may determine the amount of medial movement of an intermediate screw to achieve alignment to achieve the computed corrected geometry of the spine.

A determination of one or more bends in one or more rods to achieve the selected locations may be made in block 740. The determination of whether one or more rods is needed may be based upon the number of screws and/or the spacing of the screws. For example, a left and right set of screws and, therefore, a left and right rod to interconnect the respective screws may be determined. Further, the rod may include a selected number of bends to achieve the final selected locations of the screws which may be determined in block 740. For example, a spline determination of the final shape of the spine may be used to define a spline shape of the rod to interconnect the screw in the selected shape. Accordingly, the definition of the rod to achieve the final shape may be used to determine the number of bends and/or location of the bends in the one or more rods to achieve the selected final location of the screw.

It is further understood, however, that the implantation of the rod may include movement of the rod once the rod is positioned within the head of the screws. The determined bends in the rod may not align with a final position of the screws, but may be based upon a current position wherein the rod will be rotated or moved to achieve movement of the screws during implantation. Accordingly, the determination of the bends in the rods and/or their locations may be determined by the processor system 56 by defining the rod in an appropriate manner, such as with a spine determination between a plurality of points, such as the positions or intermediate positions between the screws and the registered image 650, to achieve the selected final geometry of the spine.

Thus, the final locations of the screws and the one or more rod bends in one or more rods may be made in block 730. Once the determination is made in block 730, the rod(s) geometry (including one or more bends in one or more rods) may be output in block 744. Outputting the determined bend or bends may include transmitting the bends, storing the bends, or any other appropriate process based upon the determination in block 740. The process 700 may be used to determine a selected rod shape to achieve a selected or determined corrected geometry of the spine.

In various embodiments, the output determined rod bends may be used to bend a rod in block 760. The rod may be bent in any appropriate manner, such as manually with a manual rod bending device, such as by the user 24, or substantially automatically or with a robotic bending system. The rod, however, may be bent according to the output determined bends in block 760.

The bent rod from block 760 may then be implanted in block 766 into the subject 28. The rod may be implanted in any appropriate manner, such as in a non-navigated procedure, including a substantially open procedure. In various embodiments, however, the rod may be navigated such as with the instrument or tool 144. As discussed above the instrument 144 may be navigated. The subject may be registered to the image, such as the prior 3D image 300 and/or the long image 390 according to various techniques, such as those discussed above. Accordingly, the registered image 650 may also be registered to the patient 28 such as with the registration as discussed above. Further, the patient tracker 140 may be used to maintain a registration with any of the selected images based upon tracking the subject 28, even during movement of the subject 28.

The registered image 650, including representations of the locations of the screws 320, such as by the representations 656, may also be used for navigation of a rod relative to the subject 28. As the registered screws 656 may be displayed on the display device 44, an icon or a graphical representation, such as the graphical representation 180, may represent the rod relative to the screw representations 656. Returning reference to FIG. 8, for example, the representations 660, 664 of the rod may be understood to be tracked or graphical representations of navigated rods positioned or being positioned relative to the plurality of screws in the subject. Accordingly, the rod may be implanted with navigation due to the registered location of the screw relative to the subject 28, and based upon the registration as discussed above between the long image 390 and the 3D image 300.

The bent rod 330, therefore, may be implanted into the subject and a process or procedure may end in block 780. Ending a procedure may be any appropriate process such as fixing the screws to implant a rod, closing an incision of the subject, or any other appropriate ending procedure. Nevertheless, the rod may be implanted between the plurality of screws as discussed above.

Accordingly a procedure may be performed on the subject 28 and confirmed without requiring a second three-dimensional scan of the subject, to assist in reducing or minimizing radiation to the subject 28 and individuals near or adjacent the imaging system. Further the non-imaged portions may be navigated relative to the registered image portions, as discussed above, to assist in performing a navigated procedure with a tracked instrument and/or implant device. The navigated position of the implant, such as the rod, may then be displayed on the display device 44 relative to the registered image, such as with a graphic representation of the implant relative to the previously registered representations, such as the screw representation 656.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of determining a location of a component in a first image data based on a second image data, comprising:

accessing the first image data of a subject;
accessing the second image data of the subject including image data of the component;
registering the first image data to the second image data;
determining a location of the component in the second image data; and
correlating the location of the component in the second image data to the first image data based at least on the registering the first image data to the second image data;
wherein the correlating the location of the component in the second image data to the first image data allows a representation of the determined location of the component in the first image data;
wherein the representation of the determined location of the component includes, accessing parameters of the component;
generating a component projection based on the accessed parameters and the first image data;
generating a graphical representation of the component that is imaged in the accessed second image data;
superimposing the generated graphical representation on the first image data; and
displaying the superimposed generated graphical representation on the first image data.

2. The method of claim 1, wherein the second image data is acquired of the subject after the first image data such that the first image data does not include image data of the component.

3. The method of claim 2, wherein the first image data includes a 3D image of the subject;
wherein the second image data includes 2D image data of the subject;
wherein registering the first image data to the second image data further comprises:
generating a 2D projection through the 3D image;
comparing the generated 2D projection to the 2D image data; and
optimizing a similarity metric between the generated 2D projection and the 2D image data at least by altering a rotation or a translation of the 3D image when generating the 2D projection.

4. The method of claim 3, further comprising:
selecting the 2D image data to include single projections of the subject.

5. The method of claim 3, further comprising:
selecting the 2D image data to include a single stitched image formed by stitching together a plurality of projections of the subject;
wherein the plurality of projections is generated with one or more x-ray fan beams.

6. The method of claim 5, wherein determining the location of the component in the second image data comprises:
comparing the generated component projection to the 2D image data;
optimizing a component similarity metric between the generated component projection and the 2D image data at least by altering a rotation or a translation of the component when generating the component projection; and
wherein the component is separate from the subject.

7. The method of claim 1, wherein correlating the location of the component in the second image data to the first image data based at least on the registering of the first image data to the second image data further comprises:

comparing the generated component projection to the second image data; and
optimizing a similarity metric between the generated component projection and the second image data at least by altering a pose of the component when generating the generated component projection.

8. The method of claim 1, further comprising:
operating an imaging system to acquire the second image data of the subject after the component is implanted in the subject to be implanted into the subject;
wherein the component is configured to be implanted into the subject.

9. A method of determining a location of a member in a 3D image data based on a 2D image data, comprising:
accessing the 3D image data of a subject;
acquiring the 2D image data of the subject including image data of the member;
generating a 2D long view of the subject including the region of interest of the subject based on the acquired 2D image data;
registering the 3D image data to the generated 2D long view;
determining a location of the member in the generated 2D long view including accessing parameters of the member to at least assist in locating the member and generating a member projection based on the accessed parameters; and
correlating the location of the member in the generated 2D long view to the 3D image data based at least on the registering of the 3D image data to the generated 2D long view;
wherein the correlating the location of the member in the second image data to the first image data allows a representation of the determined location of the member in the first image data.

10. The method of claim 9, wherein acquiring the 2D image data of the subject further comprises:
filtering an x-ray beam into at least a fan beam; and
acquiring a plurality of projections of the subject with the fan beam along a selected axis of the subject.

11. The method of claim 10, wherein generating the 2D long view of the subject further comprises:
stitching together at least a selected sub-plurality of projections of the acquired plurality of projections of the subject.

12. The method of claim 11, wherein determining a location of a member in the generated 2D long view further comprises:
comparing a generated 2D projection and the member projection to the generated 2D long view; and
optimizing a similarity metric between the generated 2D projection and the member projection and the generated 2D long view at least by altering a rotation or a translation of the member when generating the generated member projection and the generated 2D projection;
wherein the accessed parameters are known parameters of the member relative to the 2D image data.

13. A system to evaluate an image of a subject, comprising:
an imaging system to acquire a 2D image data of the subject including a member in the subject;
a processor system operable to execute instructions for:
accessing a 3D image data of a subject;
generating a 2D view of the subject based on the acquired 2D image data;
registering the 3D image data to the generated 2D view;

accessing parameters of the member;

generating a member projection based on the accessed parameters of the member and the 2D image data;

determining a location of the member in the generated 2D view based at least on the accessed parameters of the member and the generated member projection; and correlating the location of the member in the generated 2D view to the 3D image data based at least on the registering of the 3D image data to the generated 2D view;

generating a graphical representation of the member based on the accessed parameters;

a display device operable to display the generated graphical representation of the correlated location of the member in the 3D image.

14. The system of claim 13, wherein the processor system is operable to execute further instructions for generating the 2D view as a 2D long view, comprising:

filtering an x-ray beam into a plurality of fan beams; and acquiring a plurality of projections of the subject with the plurality of fan beams oriented with different views along a selected axis of the subject.

15. The system of claim 13, wherein the imaging system comprises a slotted filter.

16. The system of claim 13, wherein the processor system is operable to execute further instructions for generating the 2D view as a 2D long view, comprising:

filtering an x-ray beam into at least one fan beam; and acquiring a plurality of projections of the subject with the fan beam along a selected axis of the subject.

17. The method of claim 16, wherein the processor system is operable to execute further instructions for generating the 2D long view, comprising:

stitching together at least a selected sub-plurality of projections of the acquired plurality of projections of the subject.

18. The method of claim 16, wherein the processor system is operable to execute further instructions to access the parameters that are known parameters of the member relative to the acquired 2D image data.

* * * * *

UNITED STATES PATENT AND TRADEMARK OFFICE
CERTIFICATE OF CORRECTION

PATENT NO. : 11,903,751 B2
APPLICATION NO. : 16/375327
DATED : February 20, 2024
INVENTOR(S) : Patrick A. Helm et al.

It is certified that error appears in the above-identified patent and that said Letters Patent is hereby corrected as shown below:

In the Specification

Column 2, Detailed Description, Line 51, Delete "imagining" and insert --imaging-- therefor Column 4, Detailed Description, Line 11, Delete "34" and insert --70-- therefor Column 4, Detailed Description, Line 20, Delete "30" and insert --60-- therefor Column 4, Detailed Description, Line 22, Delete "60," and insert --36,-- therefor Column 7, Detailed Description, Line 44 (Second Occurrence), Delete "210" and insert --214-- therefor Column 10, Detailed Description, Line 25, Delete "34," and insert --24,-- therefor Column 10, Detailed Description, Line 29, Delete "34" and insert --24-- therefor Column 10, Detailed Description, Line 33, Delete "34" and insert --24-- therefor Column 14, Detailed Description, Line 44, Delete "k." and insert --κ.-- therefor Column 16, Detailed Description, Line 6, Delete "T" and insert --$\hat{T}$-- therefor Column 17, Detailed Description, Line 28, Delete "300," and insert --28,-- therefor Column 17, Detailed Description, Line 31, Delete "450" and insert --540-- therefor Column 20, Detailed Description, Line 2, Delete "34" and insert --24-- therefor Column 20, Detailed Description, Line 59, Delete "34" and insert --24-- therefor Signed and Sealed this
Twelfth Day of November, 2024

Katherine Kelly Vidal
*Director of the United States Patent and Trademark Office*

Column 21, Detailed Description, Line 66, Delete "230" and insert --320-- therefor In the Claims Column 28, Line 12, In Claim 17, delete "method" and insert --system-- therefor Column 28, Line 18, In Claim 18, delete "method" and insert --system-- therefor